United States Patent
Xu et al.

(10) Patent No.: US 9,504,770 B2
(45) Date of Patent: *Nov. 29, 2016

(54) NATURAL TISSUE SCAFFOLDS AS TISSUE FILLERS

(71) Applicant: LifeCell Corporation, Branchburg, NJ (US)

(72) Inventors: Hui Xu, Plainsboro, NJ (US); Wenquan Sun, Warrington, PA (US); Hua Wan, Princeton, NJ (US); Rick T. Owens, Stewartsville, NJ (US)

(73) Assignee: LifeCell Corporation, Branchburg, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 14/741,653

(22) Filed: Jun. 17, 2015

(65) Prior Publication Data
US 2015/0283302 A1    Oct. 8, 2015

Related U.S. Application Data

(63) Continuation of application No. 13/560,362, filed on Jul. 27, 2012, now Pat. No. 9,089,523.

(60) Provisional application No. 61/512,610, filed on Jul. 28, 2011.

(51) Int. Cl.

| | | |
|---|---|---|
| *A61K 38/18* | (2006.01) | |
| *A61K 35/12* | (2015.01) | |
| *A61K 33/38* | (2006.01) | |
| *A61K 31/728* | (2006.01) | |
| *A61L 27/36* | (2006.01) | |
| *A61K 38/17* | (2006.01) | |
| *A61L 27/20* | (2006.01) | |
| *A61L 27/54* | (2006.01) | |
| *C08L 5/08* | (2006.01) | |
| *A61L 27/34* | (2006.01) | |

(52) U.S. Cl.
CPC .......... *A61L 27/3683* (2013.01); *A61K 31/728* (2013.01); *A61K 38/1709* (2013.01); *A61K 38/18* (2013.01); *A61L 27/20* (2013.01); *A61L 27/34* (2013.01); *A61L 27/3604* (2013.01); *A61L 27/54* (2013.01); *C08L 5/08* (2013.01); *A61L 2300/104* (2013.01); *A61L 2300/236* (2013.01); *A61L 2300/252* (2013.01)

(58) Field of Classification Search
CPC ........... A61K 31/728; A61K 38/1858; A61K 38/18; A61K 38/1825; A61K 38/1866; A61K 35/12; A61L 27/3633; A61L 27/3604; A61L 27/3683; A61L 2300/104; A61L 2300/406; A61L 2300/414
See application file for complete search history.

(56) References Cited

U.S. PATENT DOCUMENTS

| | | |
|---|---|---|
| 4,582,640 A | 4/1986 | Smestad et al. |
| 4,599,226 A | 7/1986 | Fox, Jr. et al. |
| 4,902,508 A | 2/1990 | Badylak et al. |
| 4,969,912 A | 11/1990 | Kelman et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,489,304 A | 2/1996 | Orgill et al. |
| 5,613,982 A | 3/1997 | Goldstein |
| 5,632,778 A | 5/1997 | Goldstein |
| 5,641,518 A | 6/1997 | Badylak et al. |
| 5,728,752 A | 3/1998 | Scopelianos et al. |
| 5,739,176 A | 4/1998 | Dunn et al. |
| 5,800,537 A | 9/1998 | Bell |
| 5,893,888 A | 4/1999 | Bell |
| 5,993,844 A | 11/1999 | Abraham et al. |
| 6,027,743 A | 2/2000 | Khouri et al. |
| 6,096,347 A | 8/2000 | Geddes et al. |
| 6,113,623 A | 9/2000 | Sgro |
| 6,179,872 B1 | 1/2001 | Bell et al. |
| 6,194,136 B1 | 2/2001 | Livesey et al. |

(Continued)

FOREIGN PATENT DOCUMENTS

| | | |
|---|---|---|
| WO | WO-00/16822 A1 | 3/2000 |
| WO | WO-00/47114 A1 | 8/2000 |

(Continued)

OTHER PUBLICATIONS

Ahn et al., "The past, present, and future of xenotransplantation" *Yonsei Med J.*, 45(6):1017-1024 (Dec. 31, 2004).
Allman et al., "Xenogeneic Extracellular Matrix Grafts Elicit a TH2-Restricted Immune Response" *Transplantation*, 71(11):1631-1640 (Jun. 15, 2001).
Aycock et al., "Parastomal Hernia Repair With Acellular Dermal Matrix" *J. Wound Ostomy Continence Nurs.*, 34(5):521-523 (2007).
Badylak et al., "Endothelial cell adherence to small intestinal submucosa: An acellular bioscaffold" *Biomaterials*, 20:2257-2263 (1999).
Badylak et al., "Extracellular Matrix As a Biological Scaffold Material: Structure and Function" *Acta Biomaterialia*, 5(1):1-13 (2009).

(Continued)

Primary Examiner — Frederick Krass
Assistant Examiner — Tracy Liu
(74) Attorney, Agent, or Firm — McCarter & English, LLP; Matthew R. Van Eman; Vadim Cherkasov

(57) ABSTRACT

Tissue fillers derived from decellularized tissues are provided. The tissue fillers can include acellular tissue matrices that have reduced inflammatory responses when implanted in a body. Also provided are methods of making and therapeutic uses for the tissue fillers.

18 Claims, 20 Drawing Sheets

(56) References Cited

U.S. PATENT DOCUMENTS

| | | |
|---|---|---|
| 6,232,121 B1 | 5/2001 | Keeping |
| 6,326,018 B1 | 12/2001 | Gertzman et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,509,314 B1 | 1/2003 | Ruoslahti et al. |
| 6,576,265 B1 | 6/2003 | Spievack |
| 6,666,892 B2 | 12/2003 | Hiles et al. |
| 6,933,326 B1 | 8/2005 | Griffey et al. |
| 6,969,523 B1 | 11/2005 | Mattern et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,652,077 B2 | 1/2010 | Cook et al. |
| 7,699,895 B2 | 4/2010 | Hiles et al. |
| 7,763,081 B2 | 7/2010 | Ollerenshaw et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,263,101 B2 | 9/2012 | Owens et al. |
| 8,324,449 B2 | 12/2012 | McQuillan et al. |
| 2002/0045667 A1 | 4/2002 | Baker et al. |
| 2002/0103542 A1 | 8/2002 | Bilbo |
| 2003/0035843 A1 | 2/2003 | Livesey et al. |
| 2003/0143207 A1 | 7/2003 | Livesey et al. |
| 2004/0037735 A1 | 2/2004 | DePaula et al. |
| 2004/0062882 A1 | 4/2004 | Liebmann-Vinson et al. |
| 2005/0028228 A1 | 2/2005 | McQuillan et al. |
| 2005/0159822 A1 | 7/2005 | Griffey et al. |
| 2006/0073592 A1 | 4/2006 | Sun et al. |
| 2006/0210960 A1 | 9/2006 | Livesey et al. |
| 2007/0078522 A2 | 4/2007 | Griffey et al. |
| 2007/0104759 A1 | 5/2007 | Dunn et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0188416 A1 | 8/2008 | Bernstein |
| 2008/0279939 A1 | 11/2008 | Firestone |
| 2009/0035289 A1 | 2/2009 | Wagner et al. |
| 2009/0035342 A1 | 2/2009 | Karandikar et al. |
| 2009/0130221 A1 | 5/2009 | Bolland et al. |
| 2009/0306790 A1 | 12/2009 | Sun |
| 2009/0311298 A1 | 12/2009 | Nixon et al. |
| 2009/0311785 A1 | 12/2009 | Nunez et al. |
| 2010/0021961 A1 | 1/2010 | Fujisato et al. |
| 2010/0040687 A1 | 2/2010 | Pedrozo et al. |
| 2010/0209408 A1 | 8/2010 | Stephen et al. |
| 2010/0272782 A1 | 10/2010 | Owens et al. |
| 2011/0020271 A1 | 1/2011 | Niklason et al. |
| 2012/0010728 A1 | 1/2012 | Sun et al. |
| 2012/0040013 A1 | 2/2012 | Owens et al. |
| 2012/0263763 A1 | 10/2012 | Sun et al. |
| 2013/0053960 A1 | 2/2013 | Park et al. |
| 2013/0121970 A1 | 5/2013 | Owens et al. |
| 2013/0158676 A1 | 6/2013 | Hayzlett et al. |

FOREIGN PATENT DOCUMENTS

| | | |
|---|---|---|
| WO | WO-00/56377 A1 | 9/2000 |
| WO | WO-03/017826 A2 | 3/2003 |
| WO | WO-03/032735 A1 | 4/2003 |
| WO | WO-2004/031266 A2 | 4/2004 |
| WO | WO-2005/009134 A1 | 2/2005 |
| WO | WO-2007/043513 A1 | 4/2007 |
| WO | WO-2007/048099 A2 | 4/2007 |
| WO | WO-2007/106581 A2 | 9/2007 |
| WO | WO-2007/134134 A2 | 11/2007 |
| WO | WO-2009/009620 A2 | 1/2009 |
| WO | WO-2009/047346 A1 | 4/2009 |
| WO | WO-2009/105760 A2 | 8/2009 |
| WO | WO-2010/019753 A2 | 2/2010 |
| WO | WO-2010/078353 A2 | 7/2010 |
| WO | WO-2012/142419 A1 | 10/2012 |
| WO | WO-2012/166784 A1 | 12/2012 |

OTHER PUBLICATIONS

Beniker et al., "The use of acellular dermal matrix as a scaffold for periosteum replacement" Orthopedics, 26(5 Suppl):s591-s596 (May 2003).

Brandan et al.; "Decorin, A Chondroitin/Dermatan Sulfate Proteoglycan Is Under Neural Control in Rat Skeletal Muscle"; Journal of Neuroscience Research; 32:51-59 (1992).

Bruder et al., "The Effect of Implants Loaded with Autologous Mesenchymal Stem Cells on the Healing of Canine Segmental Bone Defects" J. Bone Joint Surg., 80:985-986 (1998).

Buma et al., "Tissue engineering of the meniscus" Biomaterials, 25(9):1523-1532 (2004).

Chaplin et al., "Use of an Acellular Dermal Allograft for Dural Replacement: An Experimental Study" Neurosurgery, 45(2):320-327 (Aug. 1999).

Chen et al. "Acellular Collagen Matrix As a Possible 'Off the Shelf' Biomaterial for Urethral Repair" Urology, 54(3):407-410 (1999).

Collins et al., "Cardiac xenografts between primate species provide evidence for the importance of the $\alpha$-galactosyl determinant in hyperacute rejection" J. Immunol., 154:5500-5510 (1995).

Cortiella et al.; "Influence of Acellular Natural Lung Matrix on Murine Embryonic Stem Cell Differentiation and Tissue Formation"; Tissue Engineering; 16(8):2565-2580 (2010).

Costantino et al., "Human Dural Replacement With Acellular Dermis: Clinical Results and a Review of the Literature" Head Neck, 22:765-771 (Dec. 2000).

Dobrin et al., "Elastase, collagenase, and the biaxial elastic properties of dog carotid artery" Am. J. Physiol. Heart Circ. Physiol., 247:H124-H131 (1984).

Edel, "The use of a connective tissue graft for closure over an immediate implant covered with occlusive membrane" Clin. Oral Implants Res., 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" J. Periodontol., 71:1360-1364 (2000).

Fowler et al., "Root Coverage with an Acellular Dermal Allograft: A Three-Month Case Report" J. Contemp. Dental Pract., 1(3):1-8 (2000).

Galili et al., "Interaction Between Human Natural Anti-$\alpha$-Galactosyl Immunoglobulin G and Bacteria of the Human Flora" Infect. Immun., 56(7)1 730-1737 (1988).

Galili et al., "Interaction of the Natural Anti-Gal Antibody with $\alpha$-Galactosyl Epitopes: a Major Obstacle for Xenotransplantation in Humans" Immunology Today, 14(10):480-482 (1993).

Galili et al., "Man, Apes, and Old World Monkeys Differ from Other Mammals in the Expression of $\alpha$-Galactosyl Epitopes on Nucleated Cells" J. Biol. Chem., 263(33):17755-17762 (1988).

Gamba et al. "Experimental abdominal wall defect repaired with acellular matrix" Pediatr. Surg. Int., 18:327-331 (2002).

Gebhart et al., "A radiographical and biomechanical study of demineralized bone matrix implanted into a bone defect of rat femurs with and without bone marrow" Acta Orthop. Belg., 57(2):130-143 (1991) (Abstract).

Gouk et al.; "Alterations of Human Acellular Tissue Matrix by Gamma Irradiation: Histology, Biomechanical Property, Stability, In Vitro Cell Repopulation, and Remodeling"; J. Biomed. Mater. Res. Part B: Appl. Biomater.; 84B:205-217 (2008).

Hammond et al., "Parastomal Hernia Prevention Using a Novel Collagen Implant: A Randomised Controlled Phase 1 Study" Hernia, 12:475-481 (2008).

International Search Report and Written Opinion for International Patent Application No. PCT/US2011/049062, mailed Nov. 3, 2011.

Judge, et al., "Abdominal Wall Hernia Repair: A Comparison of Sepramesh and Parietex Composite Mesh in a Rabbit Hernia Model", Journal of the American College of Surgeons, 204(2):276-281, 2007.

Kish et al., "Acellular Dermal Matrix (AlloDerm): New Material in the Repair of Stoma Site Hernias" The American Surgeon, 71:1047-1050 (Dec. 2005).

(56) References Cited

OTHER PUBLICATIONS

Kridel et al., "Septal Perforation Repair with Acellular Human Dermal Allograft" *Arch. Otolaryngol. Head Neck Surg.*, 124:73-78 (Jan. 1998).
Laidlaw et al., "Tympanic Membrane Repair With a Dermal Allograft" *Laryngoscope*, 111:702-707 (Apr. 2001).
Lee et al., "In vitro evaluation of a poly(lactide-*co*-glycolide)-collagen composite scaffold for bone regeneration" *Biomaterials*, 27:3466-3472 (2006).
Lu et al., "Novel Porous Aortic Elastin and Collagen Scaffolds for Tissue Engineering" *Biomaterials*, 25(22):5227-5237 (2004).
Ott et al.; "Regeneration and orthotopic transplantation of a bioartificial lung"; Nature Medicine—Technical Reports; 16(8):927-934 (2010).
Petersen et al.; "Tissue-Engineered Lungs for in Vivo Implantation"; Science; 329:538-541 (2010).
Simon et al., "Early failure of the tissue engineered porcine heart valve SYNERGRAFT™ in pediatric patients" *Eur. J. Cardiothorac. Surg.*, 23(6):1002-1006 (2003).
Tabata, et al., "Efficacy of a Sodium Hyaluronate-Carboxycellulose Membrane (Seprafilm) for Reducing the Risk of Early Postoperative Small Bowel Obstruction in Patients With Gynecologic Malignancies", *International Journal of Gynecological Cancer*, 20(1):188-193, 2010.
Takeuchi, et al., "A Novel Instrument and Technique for Using Seprafilm Hyaluronic Acid/Carboxymethylcellulose Membrane During Laparoscopic Myomectomy", *Journal of Laparoendoscopic & Advanced Surgical Techniques*, 16(5):497-502, 2006.
Wittmann; "How does inflammation leading to scarring differ from inflammation resolving without scars?"; FindAPhD Project Outline, University of Leeds; [http://www.findaphd.com/search/ProjectDetails.aspx?PJID=41259] [Downloaded: Sep. 5, 2013].
Yilmaz, et al., "The Effect of Seprafilm on Adhesion Formation and Tendon Healing After Flexor Tendon Repair in Chicken", *Orthopedics*, 33(3):164-170, 2010.
Zheng et al. "Porcine small intestine submucosa (SIS) is not an acellular collagenous matrix and contains porcine DNA: Possible implications in human implantation" *J. Biomed. Mater. Res. B: Appl. Biomater.*, 73(1):61-67 (2005).

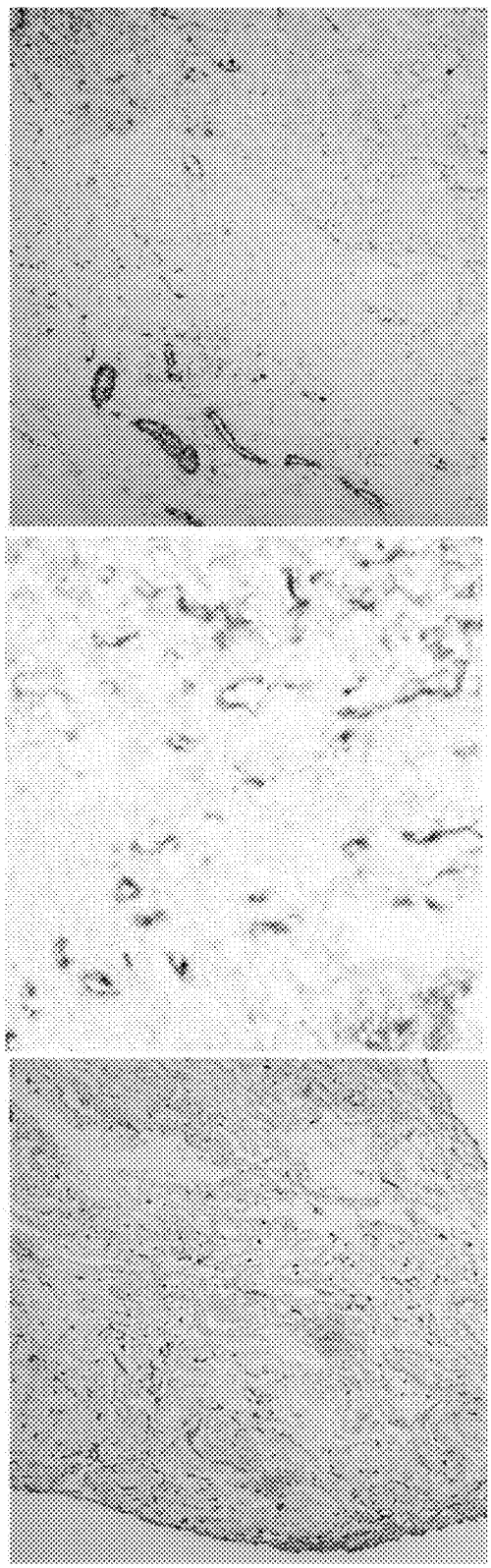

NATURAL TISSUE SCAFFOLDS AS TISSUE FILLERS

This application claims priority under 35 U.S.C. §§119-120 to U.S. patent application Ser. No. 13/560,362, which was filed on Jul. 27, 2012, and to U.S. Provisional Application No. 61/512,610, filed on Jul. 28, 2011, which are incorporated herein by reference in its entirety.

The present disclosure relates generally to tissue fillers and their use as implants and scaffolds for natural tissue regrowth after removal of a portion of native tissue.

Currently, tissue fillers are often derived from temporary hyaluronic acid or collagen-based materials. These materials lack stability and biocompatibility, and may require complex harvesting procedures. Their medical use is generally limited to temporarily filling small sites of tissue removal. Thus, existing tissue fillers are not suitable for long term removal of large volumes of tissue, such as breast lumpectomies. In addition, existing tissue fillers may not promote sufficient native tissue regrowth or limit inflammation and the formation of scar tissue. Producing a tissue filler having the texture and structural integrity of native tissue that is also capable of promoting the regrowth of native tissue while reducing inflammation and the formation of scar tissue would therefore be desirable.

Accordingly, improved tissue fillers are provided herein. In various embodiments, a tissue filler is provided, comprising an acellular tissue matrix and at least one of exogenous hyaluronic acid (HA) and exogenous decorin at a concentration sufficient to reduce an inflammatory response or fibrosis, when the tissue filler is implanted in a body. The acellular tissue matrix can be selected from an acellular lung, liver, bladder, muscle, and fat matrix. In further embodiments, the concentration of HA on the acellular tissue matrix is between approximately 0.5 mg and approximately 5.0 mg per gram of tissue filler. In further embodiments, the concentration of decorin on the acellular tissue matrix is between approximately 0.3 mg and approximately 1.0 mg per gram of tissue filler. In still further embodiments, the tissue filler elicits a reduced inflammatory response, as compared to a tissue filler lacking HA and/or decorin, when implanted in the body. In further embodiments, the tissue filler reduces fibrosis and scar tissue formation after removal of a native tissue, as compared to a tissue filler lacking HA and/or decorin, when implanted in the body.

In various embodiments, the tissue filler further comprises at least one growth factor. In further embodiments, the at least one growth factor is FGF, VEGF, PDGF, angiopoitin-2, or follistatin. In some embodiments, the tissue filler lacks substantially all alpha-galactose moieties. In certain embodiments, the tissue filler has been treated to reduce a bioburden. In further embodiments, the tissue filler is sterile.

In some embodiments, the tissue filler further comprises an antimicrobial agent. The antimicrobial agent can include at least one of CHX and silver. The CHX can be at a concentration of between approximately 0.1 mg and approximately 3.0 mg per gram of tissue filler. The silver can be at a concentration of between approximately 0.1 mg and approximately 1.0 mg per gram of tissue filler.

In various embodiments, the tissue filler is compressible. In further embodiments, the tissue filler is capable of being compressed up to approximately ⅔ of its length or width. In still further embodiments, the tissue filler is capable of returning to its original dimensions after release of compression.

In various embodiments, a method of treating a tissue after removal of native tissue is provided, comprising implanting the tissue filler described above into the tissue. In further embodiments, the implanted tissue filler can swell to fill a region of native tissue that has been removed. In still further embodiments, the implanted tissue filler is selected to have the same structural strength, texture and feel as the native tissue it replaces. In even further embodiments, implanting the tissue filler promotes the infiltration, migration, growth, and/or proliferation of surrounding native tissue cells in the tissue filler, as well as the revascularization of the tissue being treated.

In certain embodiments, the HA and/or decorin on the implanted tissue filler elicits a reduced inflammatory response, as compared to an implanted tissue filler lacking HA and/or decorin. In further embodiments, the inflammatory response is reduced by at least 10%. In still further embodiments, the HA and/or decorin on the implanted tissue filler reduces scar tissue formation after removal of a native tissue, as compared to an implanted tissue filler lacking HA and/or decorin. In even further embodiments, the decorin and/or HA remains on the tissue filler for the duration of the implant.

In some embodiments, the method of treating a tissue further comprising removing at least 20% by mass of a native tissue prior to implanting a tissue filler. In certain embodiments, the tissue being removed comprises a tumor. In some embodiments, the tissue being removed comprises breast tissue.

In various embodiments, a method of preparing a tissue filler is provided, comprising selecting a tissue, decellularizing the tissue, and contacting the tissue with least one substance that reduces inflammation and/or fibrosis when the tissue is implanted in a body. The tissue can be selected from lung, liver, bladder, muscle, and fat. In some embodiments, the at least one substance that can reduce inflammation and/or fibrosis includes at least one of hyaluronic acid (HA) and decorin. In some embodiments, when HA is used, the method includes contacting the tissue filler with a solution containing HA at a concentration of between approximately 1.0 mg/ml and approximately 10.0 mg/ml. In some embodiments, when decorin is used, the method includes contacting the tissue filler with a solution containing decorin at a concentration of between approximately 0.1 mg/ml and approximately 3.0 mg/ml.

In various embodiments, the method of preparing a tissue filler comprises contacting the tissue filler with at least one detergent. The at least one detergent can include at least one of sodium dodecyl sulfate, sodium deoxycholate, and Triton X-100. The detergent concentration and detergent exposure time can be selected to prevent removal of growth factors from the tissue filler. In some embodiments, the method of preparing a tissue filler further comprises removing alpha-galactose moieties from the tissue filler.

In some embodiments, the method of preparing a tissue filler comprises irradiating the tissue filler to reduce the bioburden of the tissue filler. Irradiation can include exposing the tissue filler to 15-17 kGy E-beam irradiation. In certain embodiments, the method further comprises sterilizing the tissue filler. In some embodiments, the method comprises contacting the tissue filler with an antimicrobial agent. The antimicrobial agent can include at least one of CHX and silver. In some embodiments, CHX is present at a concentration of between approximately 0.1 mg and approximately 3.0 mg of CHX per gram of tissue filler. In other embodiments, silver is present at a concentration of between approximately 0.1 mg and approximately 1.0 mg of silver per gram of tissue filler.

In some embodiments, the method of preparing a tissue filler comprises freeze-drying the tissue filler. In further embodiments, the method comprises rehydrating the freeze-dried tissue filler prior to implantation in a tissue.

In various embodiments, a tissue filler is provided, prepared by the methods described above.

In various embodiments, a method of treatment is provided, comprising removing a native tissue and implanting a tissue filler, wherein the tissue filler comprises an acellular tissue matrix and at least one of exogenous hyaluronic acid (HA) and exogenous decorin at a concentration sufficient to reduce an inflammatory response or fibrosis when the tissue filler is implanted in a body. In some embodiments, the native tissue being removed comprises a tumor. In certain embodiments, the native tissue is breast tissue. In some embodiments, the tissue filler used in the method of treatment is prepared according to any one of the methods described above. In some embodiments, the tissue filler used in the method of treatment comprises any one of the tissue fillers described above.

In various embodiments, a method of enhancing a native tissue is provided, comprising implanting a tissue filler into a native tissue, wherein the tissue filler comprises an acellular tissue matrix and at least one of exogenous hyaluronic acid (HA) and exogenous decorin at a concentration sufficient to reduce an inflammatory response or fibrosis when the tissue filler is implanted in a body. In further embodiments, the native tissue is breast tissue.

DESCRIPTION OF THE DRAWINGS

FIG. 18A shows immunostaining of fibroblast cells in a porcine liver tissue filler two weeks after implantation in rat. FIG. 18B shows anti-vWF immunostaining of neo-vessel formation in a porcine liver tissue filler two weeks after implantation in rat. FIG. 18C shows anti-SMC-α-actin immunostaining of myofibroblast cells in a porcine liver tissue filler two weeks after implantation in rat.

FIG. 19A shows anti-vimentin immunostaining of fibroblast cells in a porcine liver tissue filler two weeks after implantation in rat. FIG. 19B shows anti-vimentin immunostaining of fibroblast cells in a porcine liver tissue filler coated in hyaluronic acid, two weeks after implantation in rat. FIG. 19C shows anti-vimentin immunostaining of fibroblast cells in a porcine liver tissue filler coated in decorin, two weeks after implantation in rat.

DESCRIPTION OF ILLUSTRATIVE EMBODIMENTS

Figure 1A:
FIG. 1A shows fresh porcine lung stained with hematoxylin and eosin (H&E).

Reference will now be made in detail to certain exemplary embodiments according to the present disclosure, certain examples of which are illustrated in the accompanying drawings.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

In various embodiments, tissue fillers are provided. The tissue filler can comprise an acellular tissue matrix and at least one substance that can reduce inflammation and/or fibrosis when the filler is implanted in the body. The substance can be hyaluronic acid (HA) and/or decorin, at a concentration sufficient to reduce inflammation or fibrosis after implantation in the body.

The acellular tissue matrix in a tissue filler can be derived from various organ sources. Organs having a compact three dimensional shape are preferable, such as lung, liver, bladder, muscle, or fat, as they provide a spongy acellular matrix after decellularization. This spongy tissue filler can be molded and used as an implant to fill the void left by the removal of native tissue. In certain embodiments, the acellular tissue matrix is an acellular lung or liver tissue matrix. In some embodiments, the acellular tissue matrix is an acellular porcine lung or liver tissue matrix.

In various embodiments, the tissue fillers are useful as implants following removal of native tissue from a recipient organ or tissue, or as implants for cosmetic enhancement purposes. Tissue fillers derived from organs such as lung, liver, bladder, muscle, or fat provide the texture and structural strength of native tissue, while also providing a biological scaffold in which native cells and vasculature can migrate and proliferate. Furthermore, adding at least one substance such as HA and/or decorin to the acellular tissue can help reduce undesirable inflammation and/or fibrosis following implantation of a tissue filler into a recipient organ or tissue.

In certain embodiments, tissue fillers can be produced by decellularizing an organ tissue and coating the tissue in a solution containing an anti-inflammatory and/or an anti-fibrotic substance such as HA and/or decorin. In other embodiments, the presently described tissue fillers can be further processed into desired shapes and stored either fresh or freeze-dried prior to implantation in a recipient organ. The tissue fillers can be produced as aseptic or sterile materials. In some embodiments, the tissue filler is in strips, balls, or molded into other shapes that provide the desired size, shape, or structural features necessary for a given tissue filler.

As noted, the tissue fillers can comprise acellular tissue matrices, providing natural tissue scaffolds on which native tissue can grow and regenerate. As used herein, "native" cells or tissue means the cells or tissue present in the recipient organ or tissue prior to implantation of a tissue filler. Tissue fillers derived from organs having a compact three dimensional shape, such as lung, liver, bladder, muscle, or fat, are preferable as they provide a spongy acellular tissue matrix after decellularization. These spongy acellular matrices can be molded to fill the void left by removal of a native tissue while providing the texture and durability of native tissue. Furthermore, the acellular tissue matrix provides a natural tissue scaffold for native cell growth. The scaffold may consist of collagen, elastin, or other fibers, as well as proteoglycans, polysaccharides and growth factors. Tissue fillers may retain all components of the extracellular matrix, or various undesirable components may be removed by enzymatic or genetic means prior to implantation. The exact structural components of the extracellular matrix will depend on the tissue selected and the processes used to prepare the tissue scaffold. The natural tissue scaffold in a tissue filler provides a structural network of fibers, proteoglycans, polysaccharides, and growth factors on which native tissue and vasculature can migrate, grow, and proliferate.

Tissue fillers can contain acellular tissue matrices derived from various tissues and animal sources. In certain embodiments, the acellular tissue is taken from human cadaver, cow, horse, or pig. In some embodiments, tissue fillers contain acellular tissue matrices derived from lung, liver, bladder, muscle, or fat tissue in order to approximate the soft and spongy property of a native soft tissue. In some embodiments, the tissue is acellular porcine liver or lung tissue.

In various embodiments, tissue fillers comprise at least one substance that can reduce inflammation and/or fibrosis after implantation into the body (i.e., into a recipient tissue or organ), as compared to tissue matrices lacking such substances. In certain embodiments, the substance is exogenous HA and/or exogenous decorin. Decorin is a proteoglycan commonly found in connective tissue and implicated in fibrilogenesis. HA is a glycosaminoglycan commonly found in epithelial tissue. In further embodiments, the hyaluronic acid is at a concentration of, e.g., 0.5, 1.0, 1.5, 2.0, 2.5, 3.0, 3.5, 4.0, 4.5, or 5.0 mg of hyaluronic acid per gram of tissue filler (or any value in between). In other embodiments, the decorin is at a concentration of, e.g., 0.3, 0.35, 0.4, 0.45, 0.5, 0.55, 0.6, 0.65, 0.7, 0.75, 0.8, 0.85, 0.9, 0.95, or 1.0 mg of decorin per gram of tissue filler (or any value in between). In some embodiments, tissue fillers containing decorin and/or HA can reduce inflammation and/or fibrosis after implantation in a recipient tissue, as compared to an implanted tissue filler lacking HA and/or decorin.

In some embodiments, the tissue fillers contain natural tissue scaffolds, and these can be used to replace the tissue scaffold lost after removal of native tissue. Any natural tissue scaffold can be used that approximates the consistency, texture, or structural integrity of the native tissue that it is replacing. The texture and structural properties of a given tissue filler will depend on the tissue source selected, as well as on the method chosen to process the harvested tissue. In various embodiments, lung, liver, bladder, muscle, or fat tissue is used to provide effective natural tissue scaffolds because they provide the consistency, biocompatibility, and structural integrity of native tissue. In some embodiments, lung or liver tissue is used.

Figure 3B:
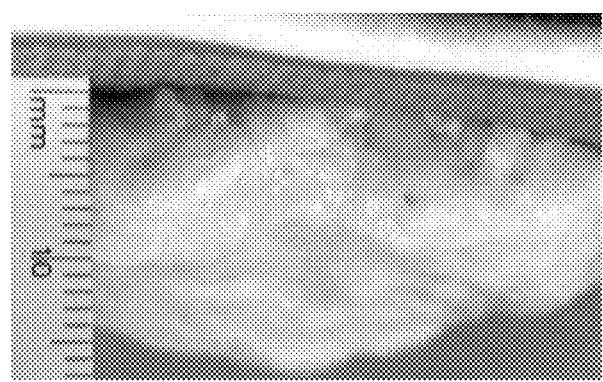
FIG. 3B is an illustration of the elasticity of acellular porcine lung after the release of compression.
Figure 3A:
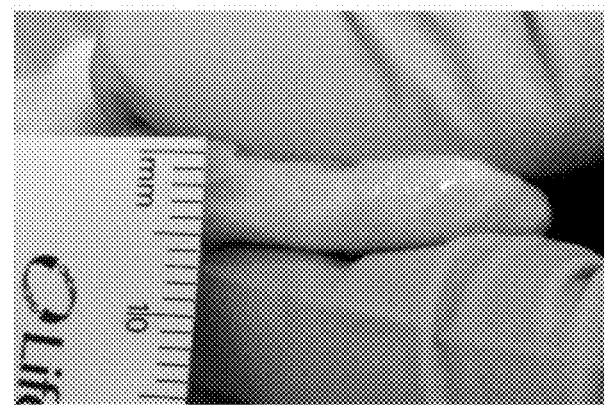
FIG. 3A is an illustration of the compressibility of acellular porcine lung.

In various embodiments, the tissue fillers are compressible. For example, the tissue fillers may be compressed up to approximately ⅔ of their initial length or width. In still further embodiments, the tissue filler is capable of returning to its original dimensions after the release of compression. In even further embodiments, a tissue filler derived from decellularized porcine lung is capable of being compressed up to approximately ⅔ of its length or width and then returning to substantially the same original dimensions after the release of compression (see FIG. 3). In various embodiments, lung or liver tissue is used as a tissue filler because, after decellularization and subsequent processing (as described below), the filler exhibits substantial ability to stretch or compress.

Tissue fillers derived from lung and liver contain abundant glycosaminoglycans when compared to other porcine tissues. In addition, in certain embodiments, tissue fillers derived from lung and liver tissue retain the major growth factors present in unprocessed lung or liver tissue. For example, lung and liver tissue fillers can retain FGF, VEGF, PDGF, angiopoitin-2 and/or follistatin (among other growth factors). In certain embodiments, 10, 20, 30, 40, 50, or 60 ng of FGF are present per gram of dried tissue filler (or any value in between). In other embodiments, 1, 2, 3, 4, 5, 6, 7, 8, 9, or 10 ng of VEGF are present per gram of dried tissue filler (or any value in between). In some embodiments, 0.5, 1.0, 1.5, or 2.0 ng of PDGF are present per gram of dried tissue filler (or any value in between). In some embodiments, 0.05, 0.1, or 0.2 ng of angiopoitin-2 are present per gram of dried tissue filler (or any value in between) where the tissue filler is made from processed lung tissue. In some embodiments, 0.5, 1.0, or 1.5 ng of follistatin are present per gram of dried tissue filler (or any value in between).

In certain embodiments, the tissue fillers lack certain antigens. For example, certain animal tissues contain alpha-galactose (α-gal) epitopes that are known to elicit reactions in humans. Therefore, tissue fillers produced from animal tissues can be produced or processed to lack certain antigens, such as α-gal. In some embodiments, tissue fillers lack substantially all α-gal moieties. Elimination of the α-gal epitopes from the natural tissue scaffold may diminish the immune response against the tissue filler, as the α-gal epitope is absent in humans. U. Galili et al., *J. Biol. Chem.* 263: 17755 (1988). Since non-primate mammals (e.g., pigs) produce α-gal epitopes, xenotransplantation of tissue filler material from these mammals into primates may result in rejection because of primate anti-Gal binding to the α-gal epitopes on the tissue filler material. The binding results in the destruction of the tissue filler material by complement fixation and by antibody-dependent cell cytotoxicity. U. Galili et al., *Immunology Today* 14: 480 (1993); M. Sandrin et al., *Proc. Natl. Acad. Sci.* USA 90: 11391 (1993); H. Good et al., *Transplant. Proc.* 24: 559 (1992); B. H. Collins et al., *J. Immunol.* 154: 5500 (1995).

As described in detail below, in various embodiments, the tissues fillers can be processed to remove antigens such as α-gal, e.g., by enzymatic treatment. Alternatively, the tissue fillers can be produced from animals that have been genetically modified to lack those epitopes.

In various embodiments, tissue fillers have reduced bioburden (i.e., a reduced number of microorganisms growing on the tissue filler). In some embodiments, tissue fillers lack substantially all bioburden (i.e., the tissue fillers are aseptic or sterile). In certain embodiments, the tissue fillers further comprise an antimicrobial agent to eliminate microbial growth and/or prevent microbial growth when implanted. The antimicrobial agent can include, for example, chlorhexidine (CHX) or silver. In certain embodiments, the concentration of CHX or silver is adjusted to remove substantially all bioburden and/or to prevent microbial growth. Effective concentrations of CHX capable of substantially reducing bioburden on tissue fillers may include 0.1 mg, 0.5 mg, 0.7 mg, 0.9 mg, 1.0 mg, 1.5 mg, 2.0 mg, 2.5 mg, or 3.0 mg per gram of tissue filler (or any value in between). Effective concentrations of silver capable of substantially reducing bioburden on tissue fillers may include 0.1 mg, 0.2 mg, 0.3 mg, 0.4 mg, 0.5 mg, 0.6 mg, 0.7 mg, 0.8 mg, 0.9 mg, or 1.0 mg per gram of tissue filler (or any value in between). As used herein, "substantially all bioburden" means tissue fillers in which the concentration of microorganisms growing on the filler is less than 1%, 0.1%, 0.01%, 0.001%, or 0.0001% of that growing on untreated fillers.

The tissue fillers, as described above, can be used after surgical removal of native tissue and/or to augment existing native tissues. In certain embodiments, the method of use comprises removing a native tissue and implanting a tissue filler. As used herein, the "native tissue" being removed can be a portion, fragment, or entirety of a tissue found in a body. The tissue filler can comprise an acellular tissue matrix and at least one substance capable of reducing inflammation and/or fibrosis. In certain embodiments, the substance is exogenous HA and/or exogenous decorin at a concentration sufficient to reduce an inflammatory response when the tissue filler is implanted in the body. In various embodiments, the tissue filler used after removal of a native tissue comprises the tissue filler described above, or is prepared as described below. In some embodiments, the tissue being removed comprises a tumor. In certain embodiments, the tissue is breast tissue.

In various embodiments, the tissue fillers described above are used after removal of a native soft tissue because they have a sponge-like consistency and can swell to fill the region of tissue that has been removed. In addition, the tissue fillers can retain the structural strength, texture, and/or feel of native soft tissue. Thus, the tissue fillers can preserve the shape of the excised natural tissue. For instance, tissue fillers derived from lung or liver can be compressed by up to approximately ⅔ of their length or width before returning to their original shape after release of the compressing force, thereby simulating the texture and elasticity of the native soft tissue that has been removed. Furthermore, in certain embodiments, tissue fillers containing anti-inflammatory and/or anti-fibrotic substances can reduce inflammation and/or scar tissue formation following implantation into a recipient organ. In various embodiments, the anti-inflammatory and/or anti-fibrotic substances are HA and/or decorin.

In certain embodiments, tissue fillers produced from lung, liver, bladder, muscle, or fat tissue are implanted after removal of native tissue. In some embodiments, these tissue fillers are rich in elastin and collagen, as well as glycosaminoglycans and growth factors. The tissue fillers thus provide natural tissue scaffolds that approximate the structure, texture, and cellular growth conditions of the tissue that has been removed. In further embodiments, porcine lung or liver tissue is used because its extracellular matrix has a well-organized sponge structure that approximates the texture of a native soft tissue.

In various embodiments, tissue fillers produced from lung, liver, bladder, muscle, or fat tissue do not elicit a significant inflammatory response when implanted in a tissue, as compared to implants derived from other tissues or from non-biologic sources. For example, tissue fillers produced from lung or liver tissue do not induce significant increases in cytokine secretion after implantation when compared tissue fillers produced from other tissue sources, such as dermis. Suitable cytokines to measure in evaluating the inflammatory response include IL-1, IL-6, IL-8, or IL-10. Similarly, any other indicator of the inflammatory response known to one of skill can be used to measure the inflammatory response. The inflammatory response can be assayed by various techniques, including in vitro incubation of tissue fillers with mononuclear blood cells or in vivo implantation of tissue fillers into a host tissue. Either method may involve cytokine immune staining or direct cytokine quantification. Other suitable techniques for assaying the inflammatory response are known in the art and may be used.

To further reduce inflammation after implantation into a recipient tissue, tissue fillers can be coated with or otherwise contain substances that reduce inflammation. As used herein, a "coated" tissue filler is one that has been contacted with an anti-inflammatory reagent or a solution containing the anti-inflammatory reagent on one or more surfaces of the tissue filler or within the tissue filler. For example, tissue fillers can be coated in decorin and/or hyaluronic acid (HA). In some embodiments, tissue fillers containing decorin and/or HA reduce inflammation after implantation in a tissue, as compared to an implanted tissue filler lacking HA and/or decorin. In further embodiments, coating a tissue filler in decorin and/or HA reduces inflammatory T cell, B cell, and/or macrophage infiltration into the tissue by 10%, 20%, 30%, 40%, 50%, 60%, 70%, or 80% (or any value in between) after implantation into a recipient organ, as compared to infiltration after an uncoated tissue filler is implanted. In further embodiments, the decorin and/or HA coating remains on the tissue filler for the duration of the implant. In still further embodiments, the coating of decorin and/or HA remains on the tissue filler 5 days, 10 days, 15 days, 20 days, or 25 days, 1 month, or 2 months (or any value in between) after implantation in a tissue.

A major challenge after removal of native tissue is the formation of undesirable scar tissue. After excision of a large volume of tissue, dense fibrosis will form due to the cross-linking of collagen during wound healing. Preventing or reducing the amount of scar tissue that forms after bulk tissue removal is therefore desirable in order to preserve the appearance and texture of the tissue. Thus, in various embodiments, tissue fillers are first coated in anti-fibrosis reagents before being implanted in a tissue, thereby reducing the amount of scar tissue formed after implantation. As used herein, a "coated" tissue filler is one that has been contacted with an anti-fibrosis reagent or a solution containing the anti-fibrosis reagent on one or more surfaces of the tissue filler or within the tissue filler.

In certain embodiments, the anti-fibrosis reagent is HA or decorin or a combination of the two. For example, decorin can stabilize the structure of native cell colonies growing in the tissue filler while preventing the infiltration of excessive fibrous connective tissue. HA and/or decorin can also reduce the inflammation caused by implantation of a tissue filler, thereby further reducing the amount of scar tissue formation. In further embodiments, coating a tissue filler in decorin and/or HA reduces fibrosis by 10%, 20%, 30%, 40%, 50%, 60%, 70%, or 80% (or any value in between) after implantation into a recipient organ, as compared to fibrosis after an uncoated tissue filler is implanted. In further embodiments, the decorin and/or HA coating remains on the tissue filler for the duration of the implant. In still further embodiments, the coating of decorin and/or HA remains on the tissue filler 5 days, 10 days, 15 days, 20 days, or 25 days, 1 month, or 2 months (or any value in between) after implantation in a tissue.

In certain embodiments, tissue fillers produced from lung or liver tissue are more resistant to collagenase digestion after implantation in a tissue when compared to tissue fillers produced from dermal tissue. Collagenases are enzymes which break the peptide bonds in collagen and can therefore degrade the extracellular matrix structures of implanted tissue fillers. Thus in some embodiments, tissue fillers produced from lung or liver tissue provide natural tissue scaffolds that retain their structural integrity and ability to promote native cell repopulation for longer periods of time after implantation when compared to tissue fillers derived from other tissue sources, such as dermal tissue.

In certain embodiments, tissue fillers retain their shape and structural integrity after implantation for one week, two weeks, three weeks, 1 month or 2 months (or any time period in between). In other embodiments, the tissue fillers retain their structural integrity for the duration of therapeutic use.

The ability of tissue fillers derived from tissue sources such as lung, liver, bladder, muscle, or fat to hold and retain desired shapes (due to their spongy extracellular matrix structure) allows for the use of tissue fillers after removal of large tissue defects (e.g., large tumor removals). For example, the removal of more than 10%, 20%, 30%, 40%, 50%, 60%, 70%, 80%, or 90% (or any percentage in-between) of a tissue mass creates a large void that requires the use of a filler to replace the lost tissue and to provide structural integrity for the remaining tissue or organ. Existing filler substances are generally used only to fill in small areas (e.g., as cosmetic fillers to remove skin wrinkles) and also lack the durability and biocompatibility needed after removal of a large volume of native tissue. In certain embodiments, a tissue filler as described above is implanted after removal of more than 10%, 20%, 30%, 40%, 50%, 60%, 70%, 80%, or 90% (or any percentage in-between) of native tissue. The spongy extracellular matrix of the tissue fillers allows them to fill the void left by the removed tissue, providing a biocompatible and durable scaffold that persists for a sufficient length of time to enable the migration and proliferation of native tissue and vasculature into the scaffold. In some embodiments, the tissue being removed and replaced with tissue filler is breast tissue. In other embodiments, the tissue being removed is muscle. In still further embodiments, the tissue being removed is liver tissue.

Tissue fillers that can provide structural support are useful to prevent visible detection of a tissue removal, i.e. for aesthetic purposes. Similarly, a tissue filler having a consistency similar to that of a removed soft tissue allows the tissue filler to provide the texture and feel the tissue had before surgical removal. For example, bulk tissue removal in breast cancer results in a disfigured breast. Implanting a tissue filler having the structural strength and elasticity of natural breast tissue can assist in breast reconstruction after surgery. Thus, in some embodiments, tissue fillers are used as implants after removal of a native soft tissue in order to retain the appearance and feel the tissue had prior to soft tissue removal. In further embodiments, the tissue removed is a tumor. In further embodiments, the tumor is a breast tumor.

In other embodiments, tissue fillers are implanted after loss or removal of large amounts of muscle tissue, for example due to muscle wasting or tumor growth. In other embodiments, tissue fillers are used as natural tissue scaffolds for liver repair or regeneration after liver resection.

In various embodiments, implanting a tissue filler can promote the repair or regeneration of a tissue after bulk tissue removal. Tissue repair or regeneration can include, for example, the infiltration of native cells from the surrounding tissue into the natural tissue scaffold of the tissue filler. Other examples of tissue repair and regeneration include the growth and proliferation of native cells in the natural tissue scaffold. In some embodiments, the tissue filler is able to support at least 50%, 60%, 70%, 80%, 90%, 95% or 99% of the cell proliferation supported by the native tissue. Still further examples of tissue repair and regeneration include revascularization of the tissue in the region where native tissue has been removed. In further embodiments, the preservation of growth factors, including FGF, VEGF, PDGF, angiopoitin-2 or follistatin (among others), in tissue fillers can enhance angiogenesis or revascularization at the implant site. In certain embodiments, implanting a tissue filler derived from lung, liver, bladder, muscle, or fat leads to fibroblast cell infiltration, growth, and/or proliferation. In further embodiments, implanting a tissue filler derived from lung, liver, bladder, muscle, or fat leads to neo-vessel formation.

In certain embodiments, tissue fillers as disclosed herein can also be used outside the reconstruction context. For example, tissue fillers can be used as implants for aesthetic enhancement purposes. Tissue fillers can be implanted into a native tissue to enhance the shape, look, or feel of a native tissue. The aesthetic tissue targets can include breast, lip, cheek, and buttocks implants, among others. In certain embodiments, implanting tissue fillers for aesthetic purposes can also lead to native tissue cell infiltration, growth, proliferation, or vascularization of the implanted tissue filler.

Production of Tissue Fillers

Tissue fillers can be produced by processing tissue from various animal sources. In certain embodiments, the tissue is taken from human cadaver, cow, horse, or pig. In some embodiments, the tissue is lung, liver, bladder, muscle, or fat tissue. In further embodiments, the tissue is porcine lung or liver tissue. In some embodiments, an entire organ is used to prepare a tissue filler. In other embodiments, portions of the organ are processed into tissue fillers. In further embodiments, the organ portions may include strips, balls, or other tissue fragments that provide the desired size, shape, or structural features necessary for a given tissue filler.

Tissue can be subjected to multiple rounds of freeze/thaw to disrupt the tissue and improve the decellularization process. In addition, bronchi or large blood vessels can be removed from tissue by manual dissection, and the tissue can be washed to remove blood cells. Any suitable washing solution can be used, including distilled water, HEPES buffer, or phosphate buffered saline, among others.

Next, the tissue is decellularized in order to remove cells from the remaining natural tissue scaffold. Various detergents can be used to decellularize, including sodium dodecyl sulfate, sodium deoxycholate, and Triton X-100. Other examples of suitable decellularization detergents and decellularization procedures are described in Cortiella et al, *Tissue Engineering* 16: 2565-2580 (2010), hereby incorporated in its entirety.

The concentration of detergent used to decellularize can be adjusted in order to preserve desirable matrix proteins and prevent protein damage during the decellularization process. The detergent may be used, for example, at a concentration of approximately 0.1%, 0.2%, 0.5%, 1%, 2%, 3%, 4%, or 5% and tissue can be incubated with detergent for 2 hours, 3 hours, 5 hours, 10 hours, 12 hours, 24 hours, 2 days, 3 days, 5 days, 7 days, 2 weeks, 3 weeks, 4 weeks, 5 weeks, or 6 weeks (or any concentration or time period in between). Appropriate concentrations and duration of detergent incubation can be adjusted depending on the detergents used and the desired harshness of decellularization.

In certain embodiments, the concentration of detergents and/or detergent incubation times are reduced in order to retain a higher level of growth factors in the extracellular matrix after decellularization. For example, a less harsh decellularization process may lead to the retention of increased levels of FGF, VEGF, PDGF, angiopoitin-2, and follistatin. In another example, the concentration of detergents and/or incubation times are increased in order to more completely remove cells from the extracellular matrix. Further, decellularization can be performed so as to remove substantially all viable cells from the extracellular matrix. As used herein, "substantially all viable cells" means tissue fillers in which the concentration of viable cells is less than 1%, 0.1%, 0.01%, 0.001%, or 0.0001% of the cells found in the tissue or organ from which the tissue filler is made.

In certain embodiments, the major growth factors present in unprocessed tissue are preserved by the decellularization process. For example, FGF, VEGF, PDGF, angiopoitin-2 and/or follistatin can be preserved in the decellularized tissue. In some embodiments, 10, 20, 30, 40, 50, or 60 ng of FGF are present after decellularization per gram of dried tissue filler (or any value in between). In some embodiments, 1.0, 2.0, 3.0, 4.0, 5.0, 6.0, 7.0, 8.0, 9.0, or 10.0 ng of VEGF are present after decellularization per gram of dried tissue filler (or any value in between). In some embodiments, 0.5, 1.0, 1.5, or 2.0 ng of PDGF are present after decellularization per gram of dried tissue filler (or any value in between). In some embodiments, 0.05, 0.1, or 0.2 ng of angiopoitin-2 are present after decellularization per gram of dried tissue filler (or any value in between) when the tissue filler is made from processed lung tissue. In some embodiments, 0.5, 1.0, or 1.5 ng of follistatin are present after decellularization per gram of dried tissue filler (or any value in between).

In various embodiments, the decellularization process does not alter the extracellular matrix of the harvested tissue. For example, the extracellular matrix in decellularized tissue can remain substantially unaltered when compared to non-decellularized tissue. The extracellular matrix can consist of collagen, elastin, fibronectin, and proteoglycans, among other extracellular proteins. In some embodiments, further proteolytic processing is employed to remove undesirable extracellular matrix components. For example, alpha-galactosidase can be applied to remove alpha-galactose moieties, as described below.

In some embodiments, after decellularization, tissue is treated with DNase to remove cellular DNA. In further embodiments, approximately 10, 20, 30, 40, or 50 units/ml of DNase are used (or any value in between). In certain embodiments, RNase is added to the DNase solution. In further embodiments, approximately 10, 20, 30, 40, or 50 units/ml of RNase are used (or any value in between). In some embodiments, at least one antibiotic is added to the DNase and/or RNase solution that is applied to decellularized tissue. Appropriate antibiotics may include, for example, gentamicin, streptomycin, penicillin, and amphotericin. In further embodiments, the antibiotic is added at a concentration of approximately 20, 30, 40, 50, 60, 70, 80, 90, or 100 μg/ml (or any value in between). In various embodiments, treatment of decellularized tissue with DNase, RNase and/or antibiotics can be for 1 hour, 2 hours, 5 hours, 12 hours, 24 hours, 2 days, 3 days, 4 days, or 5 days (or any time period in between). Appropriate duration of application and effective concentrations will depend on the type of tissue and on the DNase, RNase, and/or antibiotics selected to process the tissue.

In certain embodiments, the tissue filler is coated in at least one substance that can reduce inflammation and/or fibrosis after implantation into a recipient tissue. As used herein, "coating" a tissue filler in at least one substance means contacting one or more surfaces of the tissue filler, or an internal portion of the tissue filler, with the at least one substance, or a solution containing the substance. In further embodiments, the at least one substance is HA and/or decorin. For example, tissue fillers can be incubated in a solution containing approximately 1 mg/ml, 2 mg/ml, 3 mg/ml, 4 mg/ml, 5 mg/ml, 6 mg/ml, 7 mg/ml, 8 mg/ml, 9 mg/ml, or 10 mg/ml of hyaluronic acid (or any value in between). Incubation can be for, e.g., 1, 2, 3, 4, 5, 10, 11, 12, 13, 14, 15, 16, 17, 18, 19, 20, 21, 22, 23, 24, 30, 36, or 48 hours (or any time period in between.) After incubation, hyaluronic acid-coated tissue fillers are washed for, e.g., 1, 6, 12, 15, 20, 24, 36, or 48 hours (or any time period in between). After incubation and washing, tissue fillers are coated in hyaluronic acid at a concentration of, e.g., 0.5, 1.0, 1.5, 2.0, 2.5, 3.0, 3.5, 4.0, 4.5, or 5.0 mg of hyaluronic acid per gram of tissue filler (or any value in between). In another example, tissue fillers can be incubated in a solution containing approximately 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml, 1.5 mg/ml, 2.0 mg/ml, 2.5 mg/ml, or 3.0 mg/ml of decorin (or any value in between). Incubation can be for, e.g., 1, 2, 3, 4, 5, 10, 11, 12, 13, 14, 15, 16, 17, 18, 19, 20, 21, 22, 23, 24, 30, 36, or 48 hours (or any time period in between). After incubation, decorin-coated tissue fillers are washed for, e.g., 1, 6, 12, 15, 20, 24, 36, or 48 hours (or any time period in between). After incubation and washing, tissue fillers are coated in decorin at a concentration of, e.g., 0.3, 0.35, 0.4, 0.45, 0.5, 0.55, or 0.6 mg of decorin per gram of tissue filler (or any value in between.)

In further embodiments, tissue fillers are treated with alpha-galactosidase to remove alpha-galactose (α-gal) moieties. In some embodiments, to enzymatically remove α-gal epitopes, after washing the tissue thoroughly with saline, the tissue may be subjected to one or more enzymatic treatments to remove α-gal antigens, if present in the sample. In some embodiments, the tissue may be treated with an α-galactosidase enzyme to eliminate α-gal epitopes. In further embodiments, the tissue is treated with α-galactosidase at a concentration of 0.2 U/ml prepared in 100 mM phosphate buffered saline at pH 6.0. In other embodiments, the concentration of α-galactosidase is reduced to 0.1 U/ml or increased to 0.3 or 0.4 U/ml (or any value in between.) In other embodiments, any suitable enzyme concentration and buffer can be used as long as sufficient antigen removal is achieved. In addition, certain exemplary methods of processing tissues to reduce or remove alpha-1,3-galactose moieties are described in Xu et al., *Tissue Engineering*, Vol. 15, 1-13 (2009), which is incorporated by reference in its entirety.

Alternatively, in certain embodiments animals that have been genetically modified to lack one or more antigenic epitopes may be selected as the tissue source for a tissue filler. For example, animals (e.g., pigs) that have been genetically engineered to lack the terminal α-galactose moiety can be selected as the tissue source. For descriptions of appropriate animals, see U.S. application Ser. No. 10/896,594 and U.S. Pat. No. 6,166,288, which are incorporated herein by reference in their entirety.

In various embodiments, tissue fillers are processed to reduce bioburden (i.e., to reduce the number of microorganisms growing on the tissue filler). In some embodiments, tissue fillers are processed to remove substantially all bioburden (i.e., to sterilize the tissue filler). Suitable bioburden reduction methods are known to one of skill in the art, and may include irradiation. Irradiation may reduce or substantially eliminate bioburden. In further embodiments, 15-17 kGy E-beam radiation is used. In other embodiments, tissue fillers are coated in chlorhexidine (CHX) or silver to reduce or prevent bioburden. As used herein, "coating" a tissue filler in CHX or silver means contacting one or more surfaces of the tissue filler, or an internal portion of the filler, with CHX or silver or a solution containing CHX or silver. In certain embodiments, the concentration of CHX or silver is adjusted to remove substantially all bioburden. As used herein, "substantially all bioburden" means tissue fillers in which the concentration of microorganisms growing on the filler is less than 1%, 0.1%, 0.01%, 0.001%, or 0.0001% of that growing on untreated fillers. Effective concentrations of CHX may include 0.1 mg, 0.5 mg, 0.7 mg, 0.9 mg, 1 mg, 1.5 mg, 2.0 mg, 2.5 mg, or 3.0 mg per gram of tissue filler (or any value in between). In some embodiments, the tissue filler may be coated with a solution containing silver at any concentration between 10 μg/ml to 500 μg/ml of solution. Effective concentrations of silver may include 0.1 mg, 0.2 mg, 0.3 mg, 0.4 mg, 0.5 mg, 0.6 mg, 0.7 mg, 0.8 mg, 0.9 mg, or 1.0 mg per gram of tissue filler (or any value in between).

In various embodiments, processed tissue fillers are cut or molded into desired shapes. Shapes may be selected to conform to the contours of the tissue into which the filler will be implanted, or to conform to the contours of the void left by removal of native tissue. For example, tissue fillers may be cut into strips or molded into balls. Optimal shapes will be familiar to one of skill in the art and will depend on the specific tissue into which a filler is being implanted and on the size and/or shape of the bulk tissue that has been removed. For example, the desired shape of the tissue filler may depend on the shape and size of a tumor that has been removed from a patient.

In various embodiments, tissue fillers are cryopreserved for storage by freeze-drying. In one example, the tissue filler is placed in a cryopreservation solution that includes an organic solvent or water, to protect against damage during freeze drying. In further embodiments, following incubation in the cryopreservation solution, the tissue filler is placed in a sterile vessel that is permeable to water vapor but impermeable to bacteria. The vessel is cooled to a low temperature at a specified rate that is compatible with the specific cryoprotectant formulation to minimize the freezing damage. The tissue filler is then dried at a low temperature under vacuum conditions. At the completion of the drying, the vacuum of the freeze drying apparatus is reversed with a dry inert gas such as nitrogen, helium or argon. The tissue filler is then sealed in an impervious container and stored until use. While the example above describes one method for cryopreservation, one of skill in the art will recognize that other such methods are well known in the art and may be used to cryopreserve and store tissue fillers.

Figure 4C:
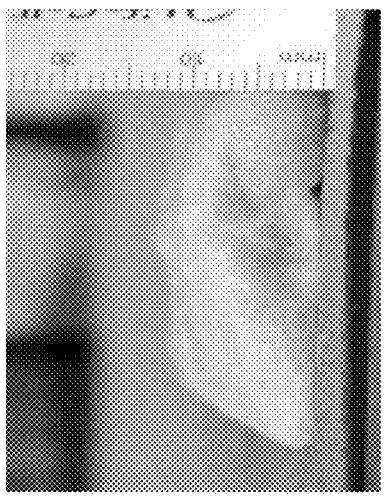
FIG. 4C illustrates the shape of a porcine lung tissue filler after rehydration.
Figure 4B:
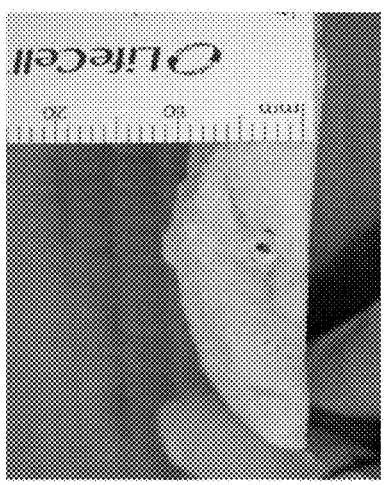
FIG. 4B illustrates the shape of a porcine lung tissue filler after freeze drying.
Figure 4A:
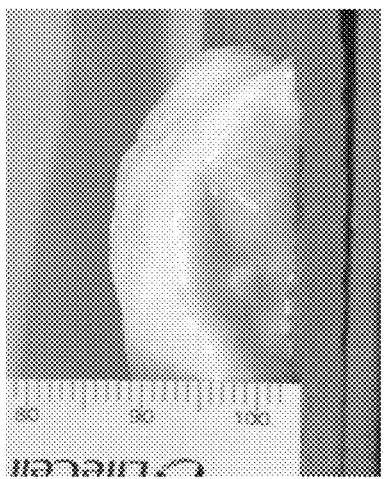
FIG. 4A illustrates the shape of a porcine lung tissue filler before freeze drying.

In some embodiments, a tissue filler that has been freeze dried is rehydrated prior to implantation in a tissue. In further embodiments, the rehydrated tissue filler retains the spongy character and also substantially the same stretchability and compressibility as found in tissue filler that has not been freeze-dried. In certain embodiments, rehydrated tissue filler derived from decellularized porcine lung retains substantially the same shape and spongy character as found in tissue filler that has not been freeze-dried (see FIG. 4).

The following examples serve to illustrate, and in no way limit, the present disclosure.

EXAMPLES

Example 1

Decellularization of Porcine Lung and Liver

To obtain lung or liver scaffolds, tissue was harvested from 3-6 month-old pigs in the slaughterhouse and shipped immediately to the laboratory for processing. Porcine tissue was freeze-thawed twice at −80° C. and then washed with distilled water for 2 days. The bronchi or large blood vessels were removed by manual dissection. Porcine lung and liver tissues were decellularized at room temperature (22 to 25° C.) for 5 days in a 10 mM HEPES buffer solution (pH 8.0) containing 2% sodium deoxycholate, 0.1% (w/v) Triton x-100 and 10 mM EDTA. Bottles were gently agitated on a shaker. Decellularized organ matrices were washed with 0.9% saline to remove detergent until foam was no longer observed in solution. Tissues were then treated at room temperature (22 to 25° C.) for 24 hours in a second HEPES buffer solution (10 mM, pH 7.4) containing 30 units/ml DNase, 50 µg/ml gentamicin, 20 mM calcium chloride and 20 mM magnesium chloride. The DNase solution was discarded, and tissue was washed three times with 0.9% saline (30 min per wash). Decellularized tissues were further treated in phosphate-buffered saline (pH 6.5) containing 0.2 unit/ml α-galactosidase and 50 mM EDTA. Tissues were sterilized with 0.1% PAA and 15-17 kGy E-beam. Tissues were stored in hydrated form or freeze-dried.

Example 2

Evaluation of Acellular Porcine Organ Matrices

Figure 1B:
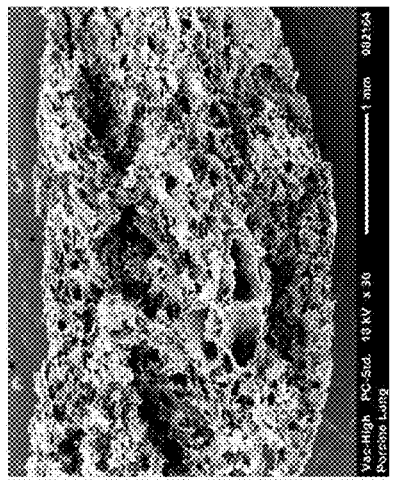
FIG. 1B shows processed porcine lung stained with H&E.
Figure 1C:
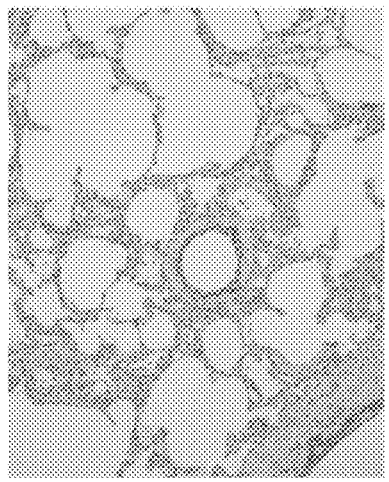
FIG. 1C shows processed porcine lung stained with Verhoeff's stain.
Figure 1D:
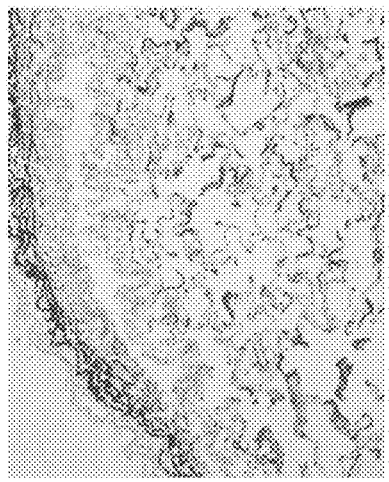
FIG. 1D is a scanning electron micrograph of processed porcine lung, as produced according to certain embodiments.

To confirm the removal of cellular components, decellularized tissues were digested with proteinase K and DNA content was measured by Quant-iT PicoGreen dsDNA Kit (Molecular Probes, Inc.), following the manufacturer's instructions. Decellularized tissues were also processed for histology (H&E, Verhoeff's, Alcian blue) and evaluated using a scanning electron micrograph (SEM). Histological evaluation (H&E stain) demonstrated that the decellularization process completely decellularized porcine organs while preserving a well-organized collagen network. FIGS. 1A & 1B show that the well-organized collagen network in porcine lung was preserved by the decellularization process. FIG. 1C shows that processed porcine lung contains abundant elastin (Verhoeff's staining) and FIG. 1D shows the well-organized sponge ultrastructure of the decellularized lung (SEM).

Figure 2A:
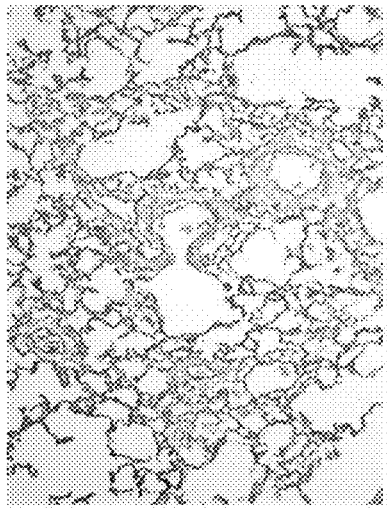
FIG. 2A shows collagen type-I immunostaining of acellular porcine lung.
Figure 2B:
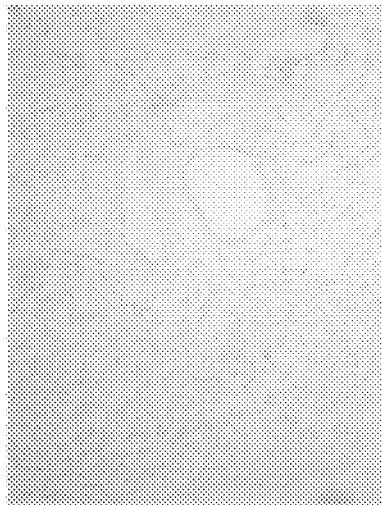
FIG. 2B shows collagen type-IV immunostaining of acellular porcine lung.
Figure 2C:
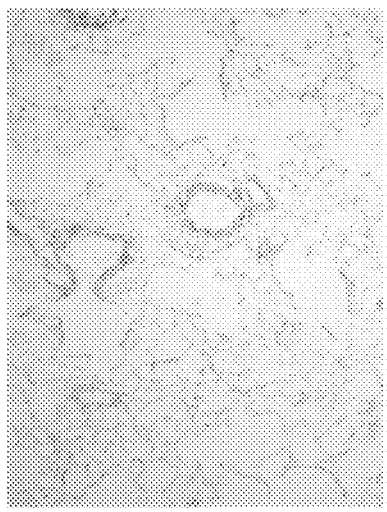
FIG. 2C shows fibronectin immunostaining of acellular porcine lung.
Figure 2D:
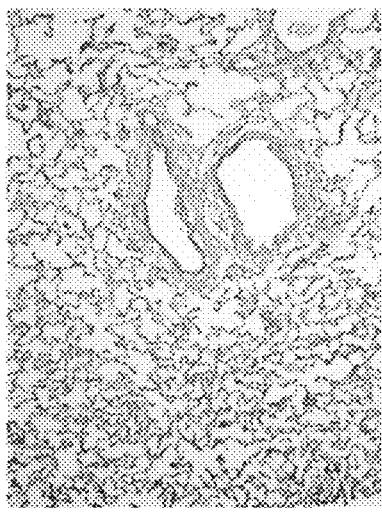
FIG. 2D shows collagen type-III immunostaining of acellular porcine lung.

To further characterize the organ matrices, extracellular matrix molecules (ECM) were measured using anti-collagen type I, III, IV, fibronectin and laminin antibodies. FIGS. 2A, 2B & 2C show that decellularized porcine lung tissue contains some type I collagen and abundant type IV collagen and fibronectin. FIG. 2D shows that type III collagen, as well as laminin (data not shown), is not a major component of the acellular lung matrix. Evaluation of fresh porcine lung tissue with the above antibodies demonstrated similar staining patterns, suggesting that the tissue processing method preserved the structure of native lung tissue matrices.

Example 3

Bioburden Quantification

TABLE 1

| Samples | CFU (Processed) | CFU (Sterilized) |
|---|---|---|
| Porcine Liver | $2.85 \times 10^4$ | 0 |
| Porcine Lung | $>10^6$ | 0 |

To ensure matrix sterility, the bioburden of tissue matrices was measured before and after a sterilization step. Table 1 shows the Bioburden quantification of acellular porcine liver and lung matrices before and after sterilization. The bioburden was extracted from tissue matrices in 50 ml saline solution followed by stomacher 400 circulator at 150 rpm for 2 minutes and collection on a 0.45 micron filter. The filter was placed on solid growth media and incubated at 37° C. for 3 days to allow for microbial colony formation. The microbial colonies were then counted to quantify the microorganisms in terms of colony forming units (CFU). Table 1 shows that no bioburden was detected after sterilization.

Acellular lung and liver matrices were also coated with the antimicrobial reagent Chlorhexidine (CHX) or silver. CHX is an antimicrobial used in many consumer products, such as mouthwash and contact lens solutions. The concentration of CHX coated on the acellular lung and liver matrices was determined by high performance liquid chromatography (HPLC) to be 1.0 mg per gram of tissue. The concentration of silver coated on the acellular matrices was determined by ICP to be 0.22 mg per gram of tissue. Tissue matrices coated with CHX were measured for bioburden. Table 2 shows that the CHX coating efficiently reduced bioburden.

TABLE 2

| Samples | CFU (Processed) | CFU (Sterilized) |
|---|---|---|
| Porcine Liver | $2.85 \times 10^4$ | 0 |
| Porcine Lung | $>10^6$ | 0 |

Example 4

Mechanical Property of Porcine Lung and Liver

The softness of acellular porcine lung or liver tissues was measured using a durometer (Table 3). A durometer measures the indentation resistance of elastomeric or soft materials based on the depth of penetration of a conical indenter. Hardness values range from 0 to 100. A lower number indicates a softer material, whereas a higher number indicates that the material is harder. The data from the durometer shows that porcine lung and liver have similar softness to human breast tissue.

TABLE 3

| Porcine muscle | Porcine liver | Porcine lung | Porcine dermis (neck) | Human breast tissue |
|---|---|---|---|---|
| 29.4 ± 4.9 (N = 4) | 2.33 ± 0.92 (n = 7) | 5.63 ± 0.91 (n = 7) | 40.0 ± 8.6 (N = 24) | 5* |

*Reference

Example 5

Tissue Integrity Testing

Figure 5:
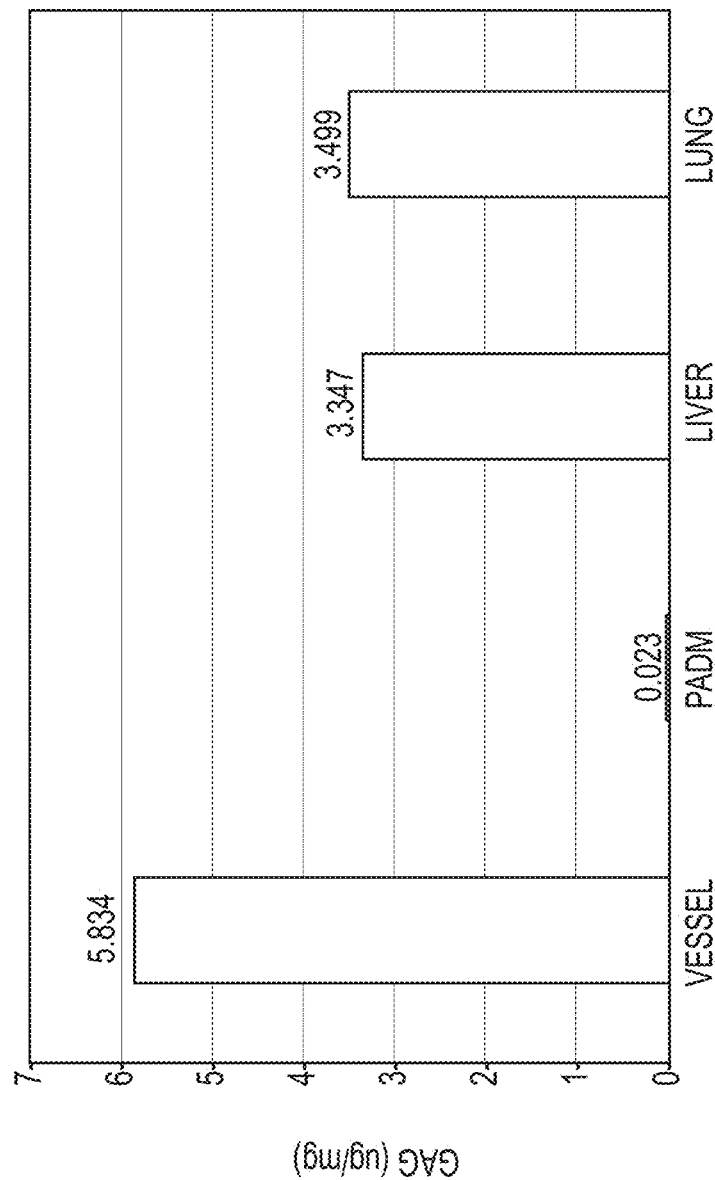
FIG. 5 is a plot of the glycosaminoglycan (GAG) concentration in extracellular matrices derived from porcine vessel, dermal, liver, and lung tissue.

To measure the retention of matrix integrity in processed lung and liver tissue, glycosaminoglycan concentrations were analyzed by a Sulfated Glycosaminoglycan Assay (Biocolor Ltd.) following the manufacturer's instructions (FIG. 5). Porcine acellular liver and lung matrices contain abundant GAG when compared to porcine acellular dermal tissue (PADM).

Figure 6:
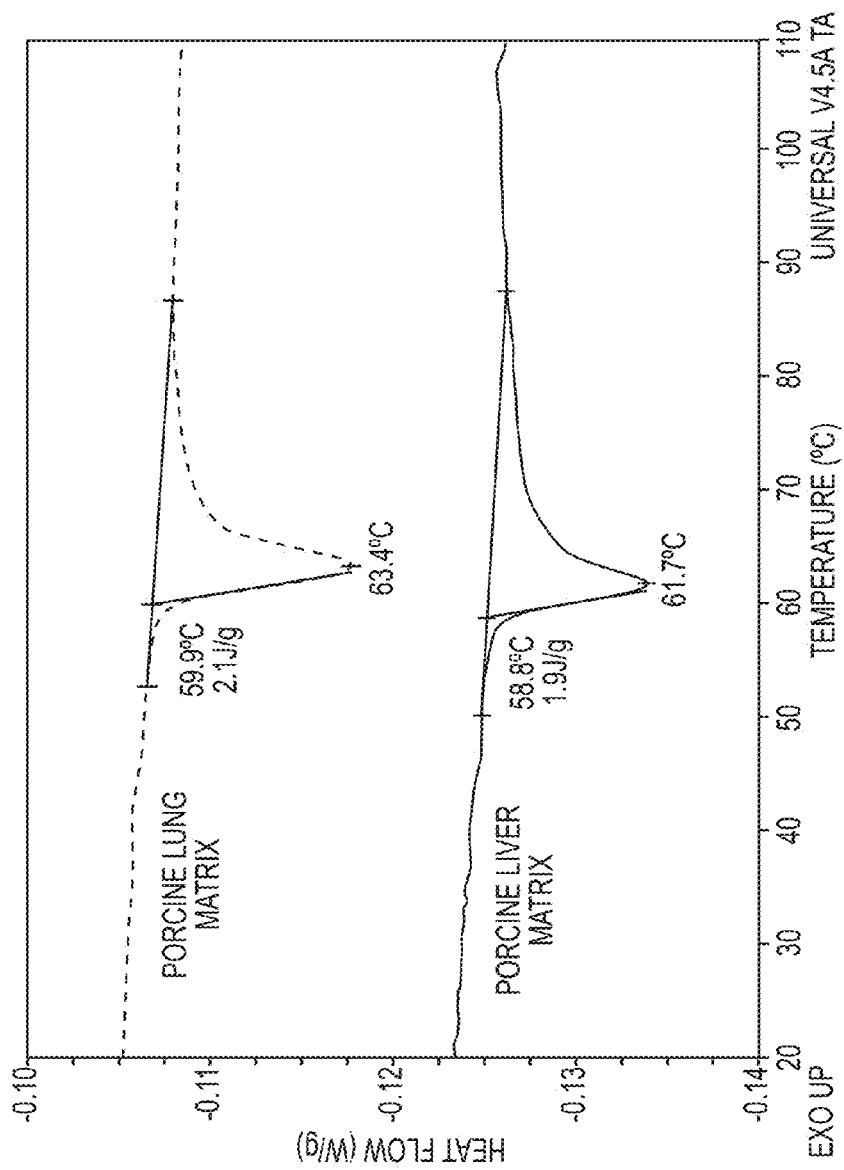
FIG. 6 shows thermogram plots for tissue fillers derived from porcine lung and liver.

The effect of tissue processing on collagen stability was measured by modulated temperature differential scanning calorimetry (TA Instruments, New Castle, Del.), as previously described. Gouk et al., *J. Biomed. Mat. Res. Part B: Appl. Biomat.* 84B: 205-217 (2007). The onset temperature ($T_m$) and enthalpy ($\Delta H$) of collagen denaturation were determined by analysis of thermograms using Universal Analysis 2000 software (version 4.0) with dry tissue samples (FIG. 6). Thermograms of both porcine lung and liver acellular tissue matrices had unfolding onset temperatures for collagen molecules around 59-60° C., and peak unfolding temperature around 62-64° C. The data demonstrate that the integrity of native lung and liver matrices is preserved after processing.

Figure 7:
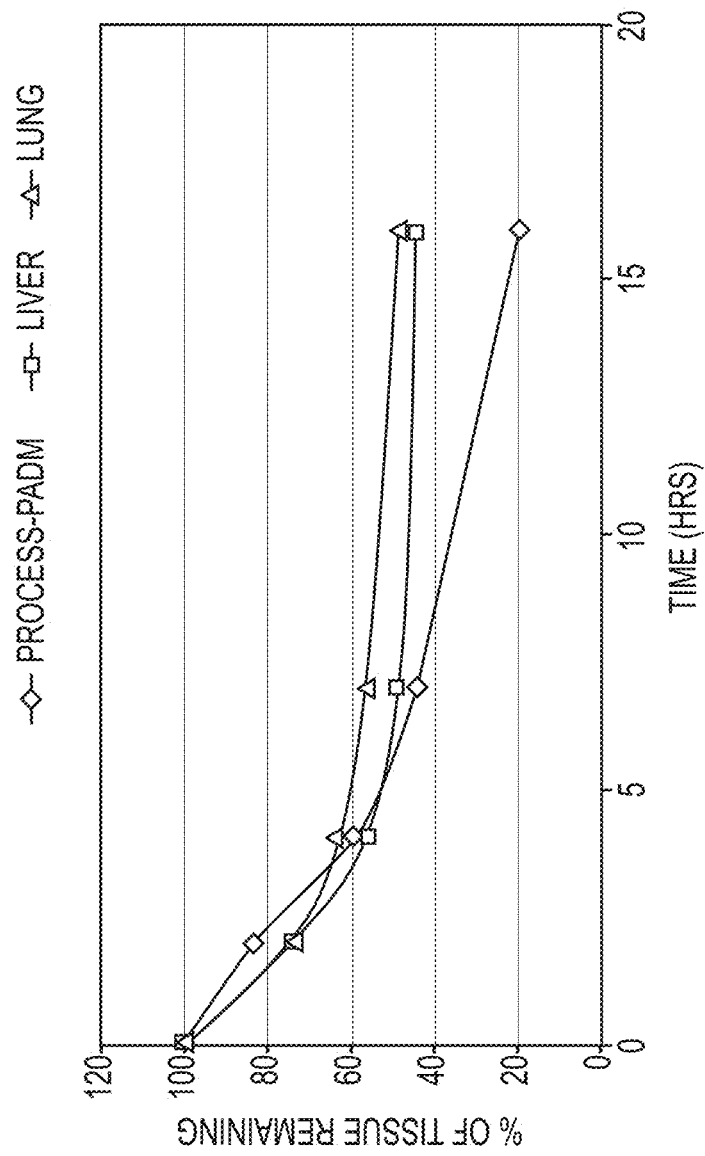
FIG. 7 is a plot showing the effect of collagenase digestion on tissue fillers derived from porcine liver, lung, and dermal tissue.

The susceptibility of collagen in lung and liver matrices to enzyme digestion was evaluated in vitro by type I collagenase (Sigma-Aldrich, St. Louis, Mo.) and proteinase K (Fisher Scientific, Fair Lawn, N.J.) following the protocol described previously (Gouk, 2007). Briefly, samples were incubated with collagenase for varying lengths of time at 37° C. The digested tissues were then washed and freeze-dried. The resistance to enzyme digestion was calculated as a percentage of the dry weight of tissue remaining at various time points (FIG. 7). FIG. 7 suggests that liver and lung acellular matrices are more resistant to collagenase digestion when compared to porcine dermal tissue.

Example 6

Anti-Fibrosis Coatings on Acellular Lung and Liver Matrices

Figures 8A, 8B:
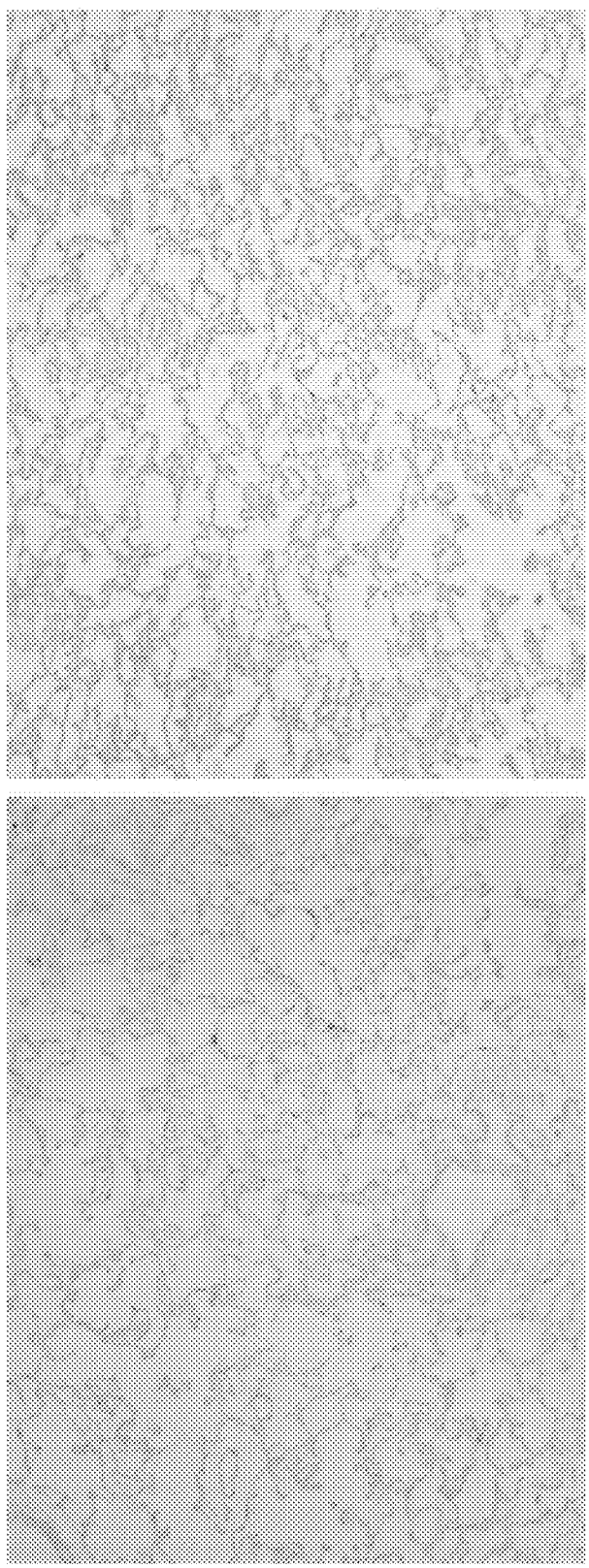
FIG. 8A shows alcian blue staining of tissue filler derived from porcine lung.
FIG. 8B shows alcian blue staining of tissue filler derived from porcine lung that is coated in hyaluronic acid.
Figure 9:
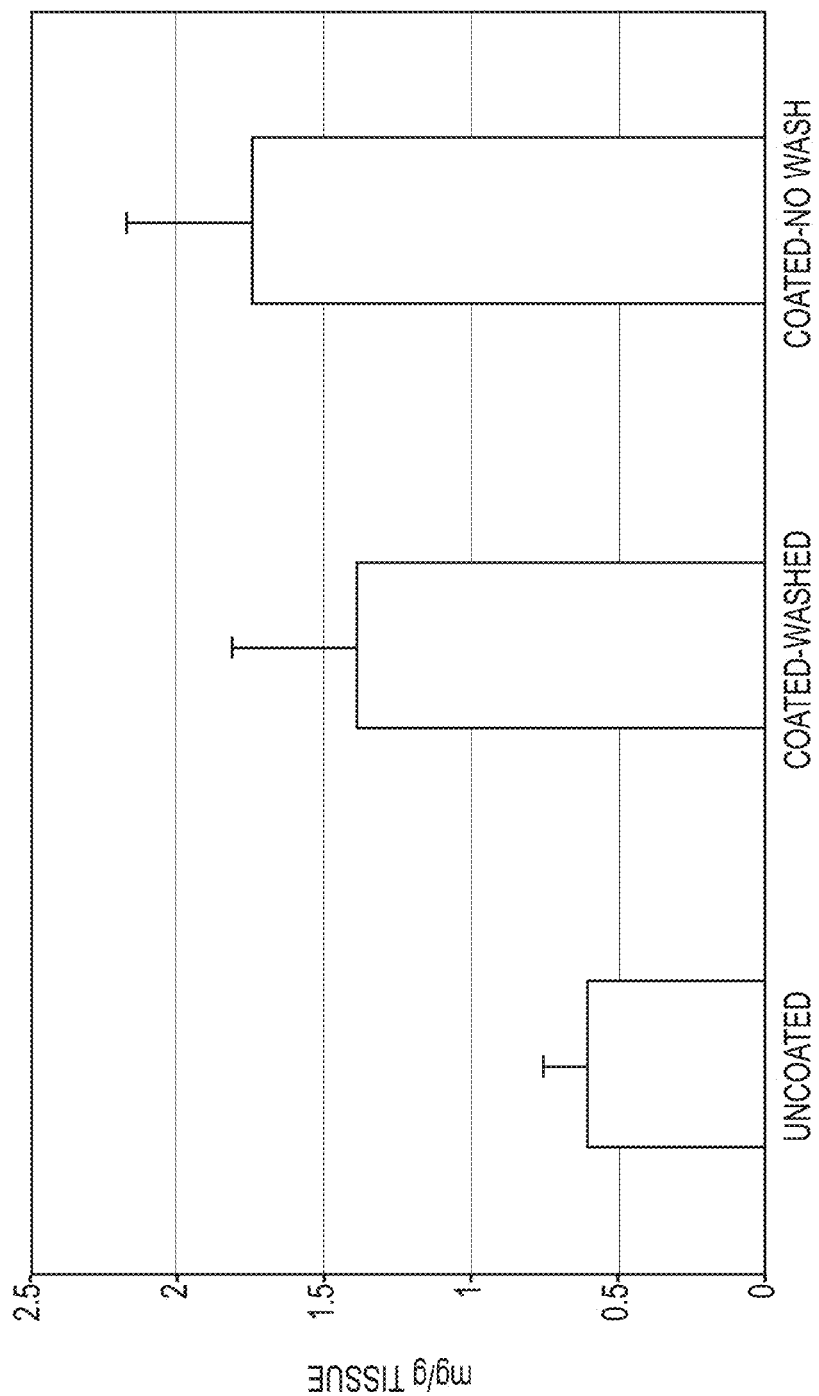
FIG. 9 is a plot showing the concentration of HA in uncoated porcine liver tissue filler (left), in porcine liver tissue filler incubated with 5 mg/ml of hyaluronic acid sodium salt (right), and in porcine liver tissue filler incubated with 5 mg/ml of hyaluronic acid sodium salt and washed overnight (center).

To reduce the possibility of fibrosis tissue formation, acellular tissue matrices were coated with anti-fibrosis reagents, such as hyaluronan or recombinant human decorin. For hyaluronan coating, tissue matrices were incubated with 5 mg/ml of hyaluronic acid (HA) sodium salt (Fluka 53747) at room temperature for 16 hours. Binding of HA to tissue matrices was confirmed by Alcian blue staining (FIG. 8). FIG. 8 shows that lung matrices were successfully coated with HA. The concentration of HA coated on the tissue matrices was determined by a DMMB colorimetric assay. Briefly, the HA coated tissue matrices were digested with collagenase and the supernatants were quantified to determine the GAG concentration using dimethylmethylene blue (DMMB) staining. FIG. 9 shows that HA was effectively coated onto the tissues and persisted after washing overnight with 3 changes.

Figures 10A, 10B, 10C:
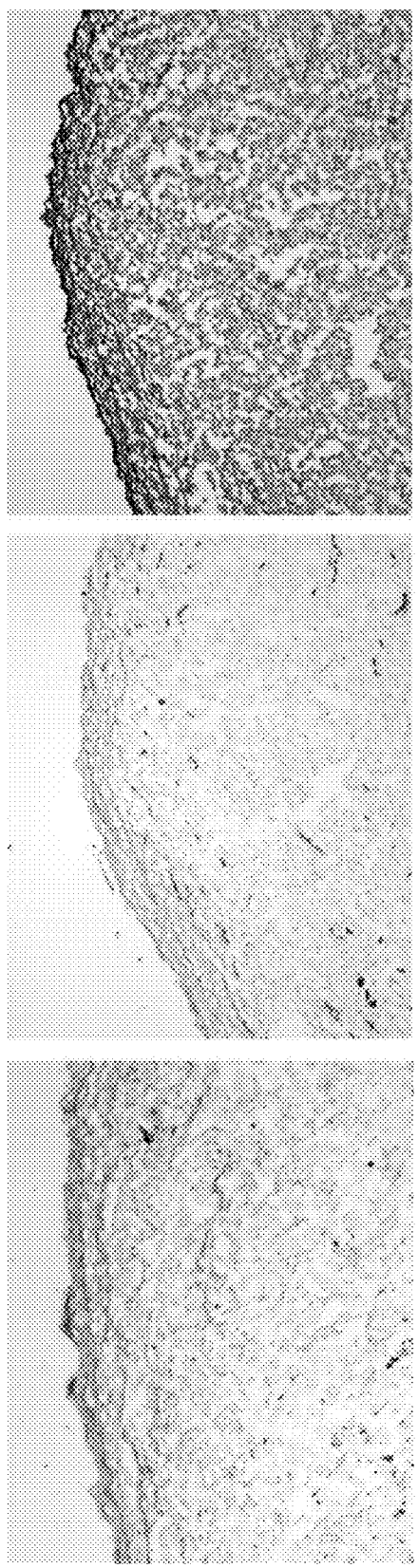
FIG. 10A shows anti-human decorin staining of tissue filler derived from porcine liver.
FIG. 10B shows control serum staining of tissue filler derived from porcine liver that is coated in human decorin.
FIG. 10C shows anti-human decorin staining of tissue filler derived from porcine liver that is coated in human decorin.
Figure 11:
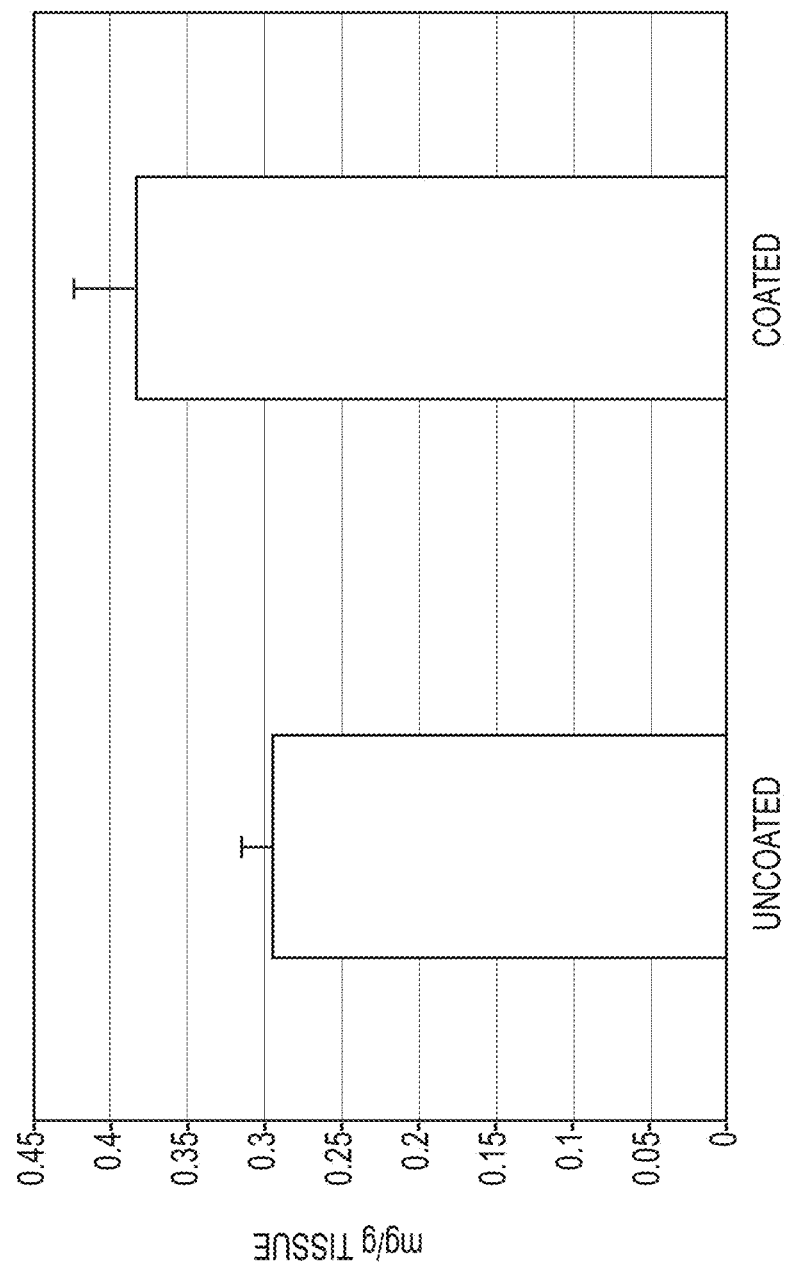
FIG. 11 is a plot showing the concentration of decorin in uncoated porcine liver tissue filler (left) and in porcine liver tissue filler incubated with 1 mg/ml of decorin and washed overnight (right).
Figure 12B:
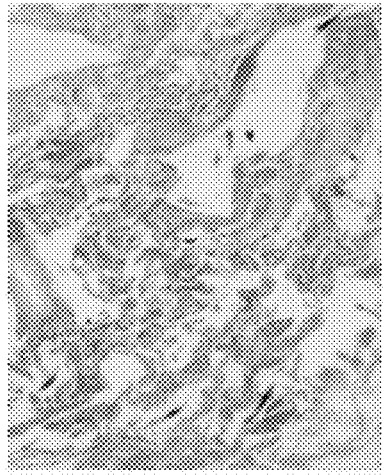
FIG. 12B is an H&E stain showing in vitro growth of rat fibroblast in tissue fillers derived from porcine liver.
Figure 12D:
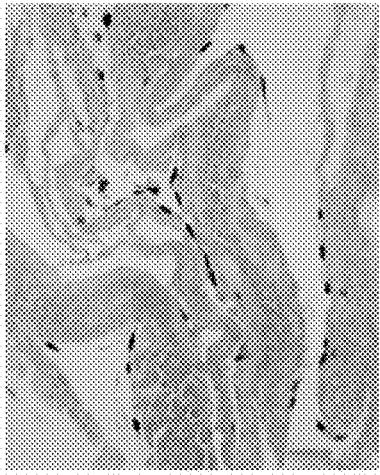
FIG. 12D is an H&E stain showing in vitro growth of rat stem cells in tissue fillers derived from porcine liver.
Figure 12A:
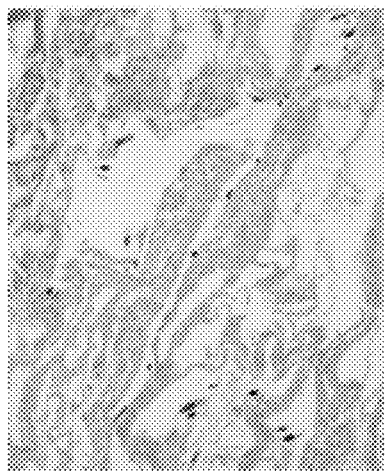
FIG. 12A is an H&E stain showing in vitro growth of rat fibroblast in tissue fillers derived from porcine lung.
Figure 12C:
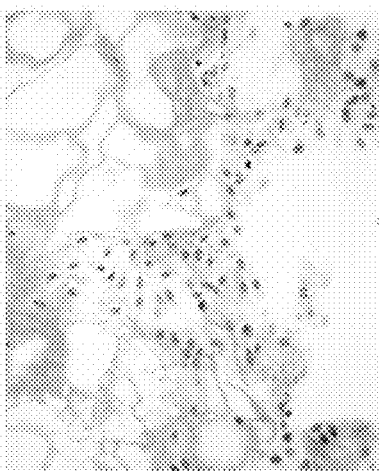
FIG. 12C is an H&E stain showing in vitro growth of rat stem cells in tissue fillers derived from porcine lung.

For decorin coating, tissue matrices were incubated with 1 mg/ml of recombinant human decorin (DCN) at room temperature for 16 hours and then washed overnight to remove unbound decorin. Binding of human decorin to the tissue matrices was confirmed by an anti-human decorin antibody that does not react with porcine decorin (FIG. 10). The decorin concentration coated on the tissue was determined with a RayBio Human Decorin ELISA kit (Ray Biotech Inc). FIG. 11 shows that human decorin was effectively coated onto liver matrices and persisted after washing overnight with 3 changes.

Example 7

In Vitro Cell Growth and Inflammation

Both rat fibroblast cells (ATCC, CRL-1213) and human fibroblast cells (ATCC, CRL-2522) were cultured in minimal essential medium (MEM) supplemented with 10% fetal bovine serum (ATCC, MD). Human monocytes were cultured in macrophage-serum-free medium (SFM) (Gibco, CA). Rat bone marrow or adipose mesenchymal stem cells (MSC) were cultured in MSC expansion medium (Millipore, MA). Acellular lung and liver tissues were washed in saline (supplemented with 50 µg/ml gentamicin) for 12 hours with shaking at room temperature (6 changes) and then placed at the bottoms of the wells in 24-well plates (0.5×0.5 cm of tissue per well). One milliliter of cells ($5$-$10 \times 10^4$ cells/ml) was applied to the tissues. Co-cultures of tissues with cells were then fixed and stained for H&E at 1, 2 and 3 weeks of culture. FIG. 12 shows that porcine lung and liver matrices support growth, migration and proliferation of rat MSC and fibroblast cells.

Figure 13:
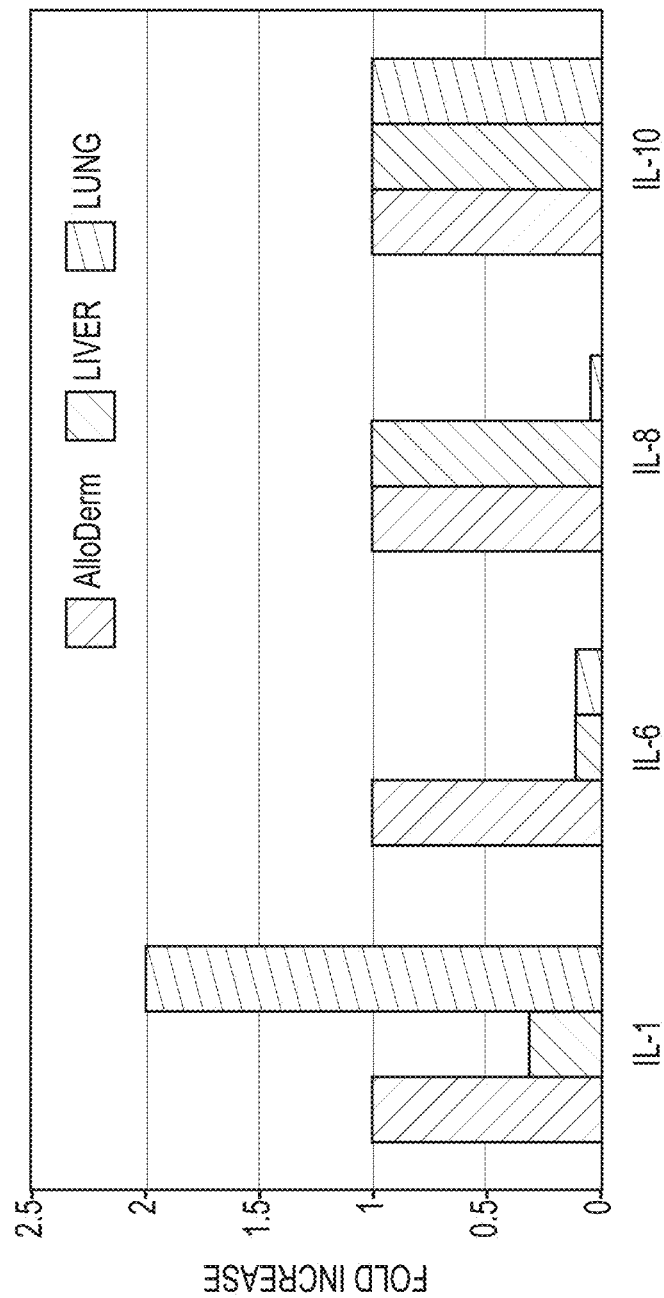
FIG. 13 illustrates inflammatory cytokine levels induced by in vitro culturing of human blood mononuclear cells with tissue fillers derived from porcine lung, liver and dermal tissue.
Figure 14A:
FIG. 14A illustrates the gross morphology of tissue fillers derived from porcine lung two weeks after implantation in rat.
Figure 14E:
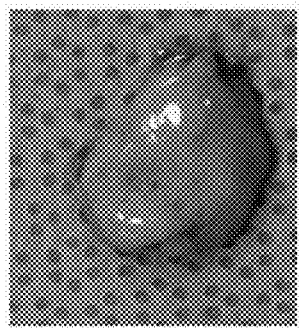
FIG. 14E illustrates the gross morphology of tissue fillers derived from porcine liver and coated in decorin, two weeks after implantation in rat.
Figure 14D:
FIG. 14D illustrates the gross morphology of tissue fillers derived from porcine liver and coated in hyaluronic acid, two weeks after implantation in rat.
Figure 14C:
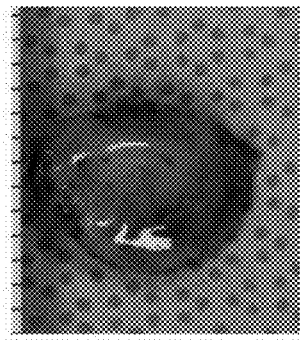
FIG. 14C illustrates the gross morphology of tissue fillers derived from porcine liver and coated in CHX, two weeks after implantation in rat.
Figure 14B:
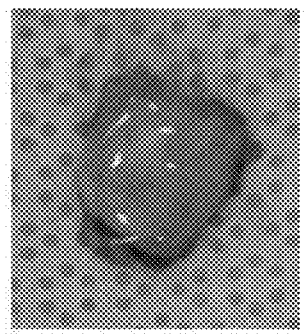
FIG. 14B illustrates the gross morphology of tissue fillers derived from porcine liver two weeks after implantation in rat.
Figure 15A:
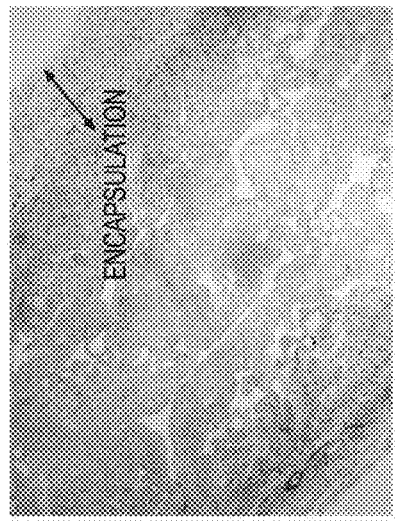
FIG. 15A shows H&E staining of tissue fillers derived from porcine liver.
Figure 15B:
FIG. 15B shows H&E staining of tissue fillers derived from porcine liver coated in chlorhexidine (CHX).
Figure 15C:
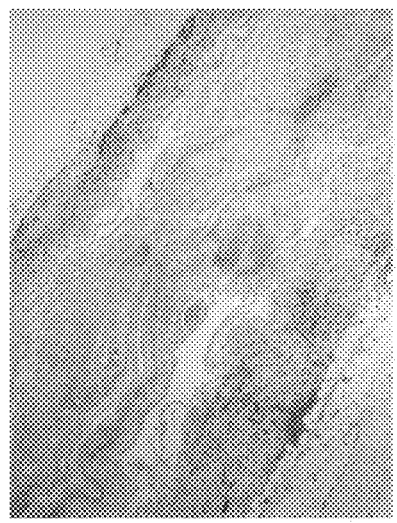
FIG. 15C shows H&E staining of tissue fillers derived from porcine liver coated in hyaluronic acid.
Figure 15D:
FIG. 15D shows H&E staining of tissue fillers derived from porcine liver coated in decorin.
Figure 16A:
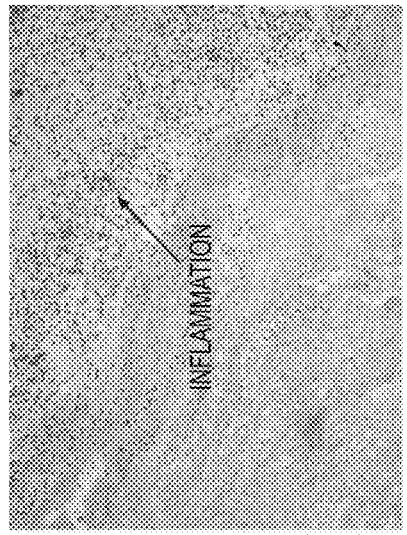
FIG. 16A shows H&E staining of tissue fillers derived from porcine liver.
Figure 16B:
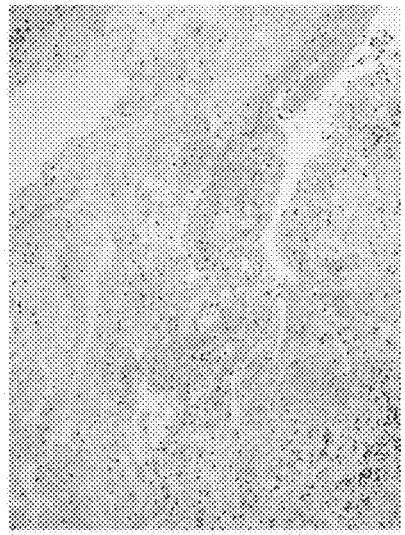
FIG. 16B shows H&E staining of tissue fillers derived from porcine liver coated in chlorhexidine (CHX).
Figure 16C:
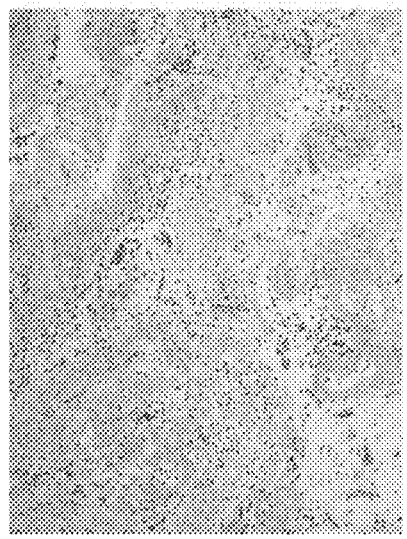
FIG. 16C shows H&E staining of tissue fillers derived from porcine liver coated in hyaluronic acid.
Figure 16D:
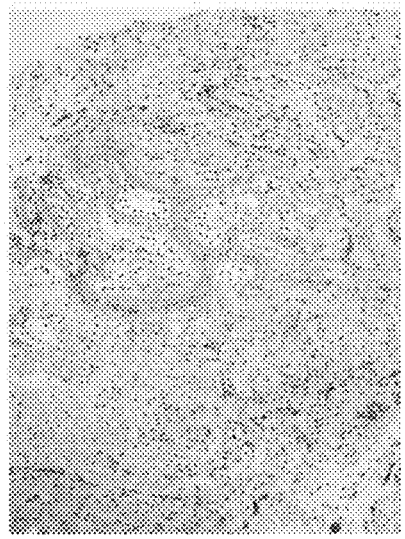
FIG. 16D shows H&E staining of tissue fillers derived from porcine liver coated in decorin.

Fresh human mononuclear cells were isolated from human donor blood by Ficoll separation. One million cells in 1 ml macrophage-SFM (Gibco, CA) were applied to acellular tissue matrices (0.5×0.5 cm) placed at the bottoms of the wells in 24-well plates. The culture supernatant was collected 7 days post co-culture and centrifuged. The supernatant was analyzed for cytokines (IL-1, -2, -4, -6, -8, -10, IFN-g and TNF-a) with an Elisa kit for human cytokines. FIG. 13 shows that porcine liver and lung matrices did not induce significant inflammatory cytokines when the matrices were cultured with human blood mononuclear cells.

Example 8

Growth Factors in Processed Lung or Liver Tissue Matrices

Growth factors retained in processed lung and liver tissue matrices were determined using a Bio-Plex Pro Assay (Bio-Rad). Briefly, processed tissue was washed with saline and then freeze-dried and cryo-milled. Cryo-milled tissue (100 mg) was extracted in 1 ml tissue extraction reagent I (invitrogen) at 4° C. overnight. The supernatant was used for Bio-Plex Pro Assays (Human Angiogenesis Panel). The data shows that the decellularizing and processing of lung and liver tissues preserve the key growth factors (FGF, VEGF, PDGF) found in porcine organ matrices (table 4).

TABLE 4

| ng/g dried tissue | FGF | VEGF | PDGF | Angiopoitin-2 | Follistatin |
|---|---|---|---|---|---|
| Processed Liver | 18.43 | 2.04 | 0.72 | undetectable | 0.72 |
| Processed Lung | 42.7 | 8.44 | 1.89 | 0.11 | 0.58 |

Example 9

In Vivo Testing

To assess the biological response to processed tissue matrices in vivo, processed porcine lung and liver tissue matrices (1.0×1.0×0.5 cm) were subcutaneously implanted in rats for 14 days. Processed acellular matrices were compared to matrices coated with an anti-microbial agent, HA, or human decorin. The explants were grossly evaluated for their shape, hardness, and size (Table 5 & FIG. 14). After two weeks, implanted porcine lung matrices had the same shape, size and sponge property as observed prior to implantation. CHX-coated liver tissue matrices were firm and seemed encapsulated, while HA or decorin-coated liver tissue matrices were soft with less surrounding connective tissues.

TABLE 5

Gross observation of the explants

| Explants | Shape change | Hardness | Size |
|---|---|---|---|
| Liver matrix | No | Slightly firm | 1 × 1 × 0.6 cm |
| Liver-CHX | No | Firm | 1.5 × 1 × 0.8 cm |
| Liver-HA | No | Soft | 1 × 1 × 0.8 cm |
| Liver-Decorin | No | Soft | 1 × 1 × 0.8 cm |

Figure 17B:
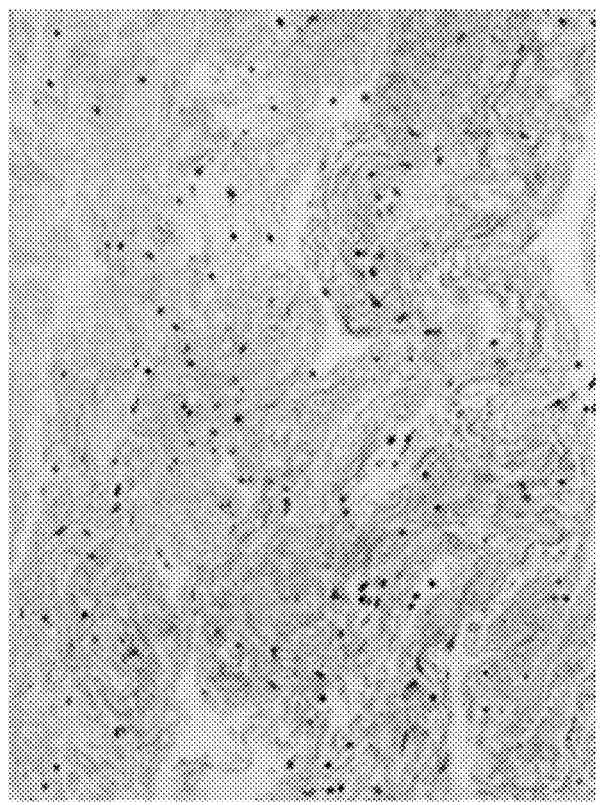
FIG. 17B shows H&E staining of tissue fillers derived from porcine liver coated in decorin.
Figure 17A:
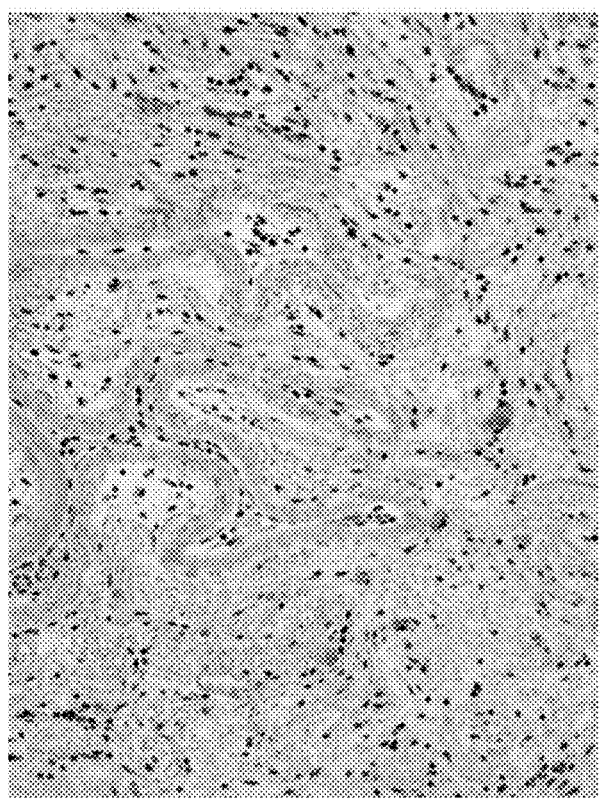
FIG. 17A shows H&E staining of tissue fillers derived from porcine liver coated in HA.

The processed porcine lung and liver tissue matrix explants were also evaluated histologically for cell infiltration, inflammation and encapsulation. Histology demonstrated cellular infiltration in all grafts. Matrices coated with CHX appeared to be encapsulated and showed less fibroblast cell repopulation (FIG. 15). Matrices coated with HA and decorin had minimal inflammation (FIG. 16). This data suggests that coating matrices in HA and human decorin reduces inflammation and encapsulation. Histology also demonstrated cellular repopulation and revascularization in the implanted matrices. Human decorin-coated grafts appeared to have fewer fibroblast cells than did the uncoated or HA-coated grafts, indicating regulatory effects of decorin on fibroblast proliferation (FIG. 17).

To assess the host biological response to the implants, two week explants of acellular liver matrix grafts were immunostained with anti-vimentin to detect fibroblasts, anti-vWF to detect neo-vessel formation, and anti-alpha-smooth muscle cell actin to detect myofibroblast cells (myofibroblast cells have been reported to be involve in fibrosis formation). Fibroblast cell repopulation was confirmed by immunostaining and neo-vessel formation was shown by vWF staining (FIGS. 18A & B). SMC-α-Actin staining did not suggest induction of myofibroblast cells (FIG. 18C). The grafts coated with human decorin appeared to have fewer fibroblast cells when compared to non-coated or HA-coated grafts (FIG. 19).

To further characterize the inflammatory cells in the liver and lung grafts, T cells, B cells and Macrophages at the graft site were stained using antibodies. The level of inflammation was scored as follows: 0=none, 1=mild, 2 moderate, 3=significant. The data in Table 6 indicate that the porcine acellular lung and liver matrices do not induce significant inflammation in a rat subcutaneous implantation model.

TABLE 6

|  | T cells | B cells | Macrophages |
|---|---|---|---|
| Lung | 1 | 1 | 1 |
| Lung-HA | 0.5 | 0.5 | 0.5 |
| Lung-decorin | 0.5 | 0.5 | 0.5 |
| Liver | 1 | 1 | 1 |
| Liver-HA | 0.5 | 0.5 | 0.5 |
| Liver-decorin | 0.5 | 0.5 | 0.5 |

Figure 20C:
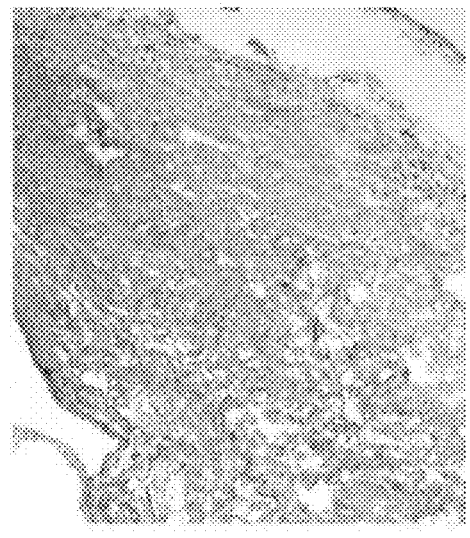
FIG. 20C shows anti-human decorin immunostaining of a tissue filler derived from porcine liver and coated in human decorin, two weeks after implantation in rat.
Figure 20B:
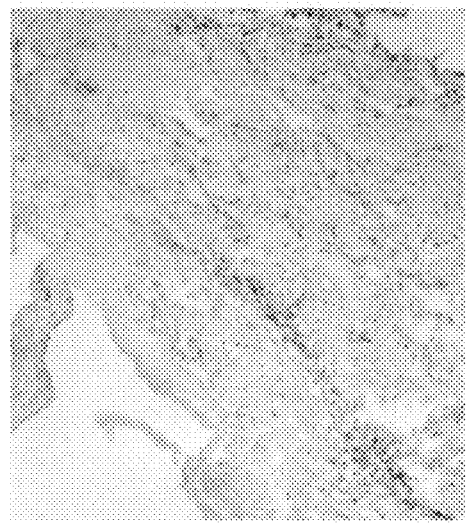
FIG. 20B shows control serum staining of tissue fillers derived from porcine liver coated in human decorin, two weeks after implantation in rat.
Figure 20A:
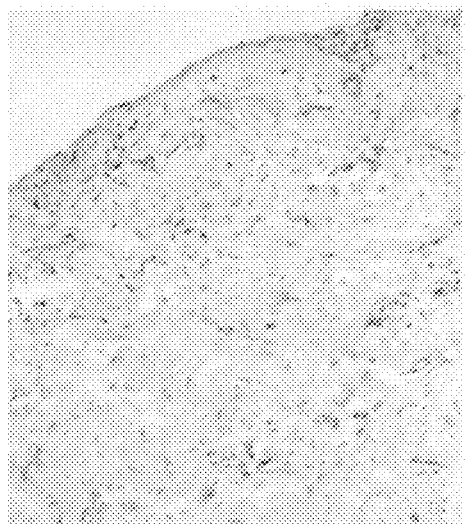
FIG. 20A shows anti-human decorin immunostaining of tissue fillers derived from porcine liver two weeks after implantation in rat.

To assess if coated decorin remained on acellular matrices over time, acellular liver matrices coated with decorin were stained with anti-human decorin antibody two weeks after rat subcutaneous implantation (FIG. 20). The results suggest that coated human decorin was present on the implant 2-weeks post-implantation.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A tissue filler, comprising:
   an acellular tissue matrix having a stable three-dimensional structure, having the ability to maintain the same shape, size, and sponge property after being implanted for two weeks as was observed prior to implantation; and
   at least one of exogenous hyaluronic acid (HA) and exogenous decorin on a surface of the acellular tissue matrix at a concentration which reduces an inflammatory response or fibrosis when the tissue filler is implanted in a body as compared to the same tissue filler not comprising hyaluronic acid or decorin.

2. The tissue filler of claim 1, wherein a concentration of HA on the acellular tissue matrix is between approximately 0.5 mg and approximately 5.0 mg per gram of tissue filler.

3. The tissue filler of claim 1, further comprising at least one growth factor.

4. The tissue filler of claim 3, wherein the at least one growth factor is selected from at least one of FGF, VEGF, PDGF, Angiopoitin-2, or Follistatin.

5. The tissue filler of claim 1, wherein the tissue filler has been treated to reduce a bioburden.

6. The tissue filler of claim 1, further comprising an antimicrobial agent.

7. The tissue filler of claim 6, wherein the antimicrobial agent includes at least one of chlorhexidine (CHX) and silver.

8. The tissue filler of claim 7, wherein the CHX has a concentration between approximately 0.1 mg and approximately 3.0 mg per gram of tissue filler.

9. The tissue filler of claim 8, wherein the silver has a concentration between approximately 0.1 mg and approximately 1.0 mg per gram of tissue filler.

10. The tissue filler of claim 1, wherein the tissue filler is capable of being compressed up to approximately ⅔ of its length or width.

11. The tissue filler of claim 10, wherein the tissue filler is capable of returning to its original dimensions after release of compression.

12. The tissue filler of claim 1, wherein a concentration of decorin on the acellular tissue matrix is between approximately 0.3 mg and approximately 1.0 mg per gram of tissue filler.

13. The tissue filler of claim 1, wherein the acellular tissue matrix comprises a dermal matrix.

14. A method of treating a tissue site, comprising:
selecting a tissue site; and
implanting the tissue filler of claim 1 in the tissue site.

15. A tissue filler, comprising:
an acellular tissue matrix having a stable three-dimensional structure, having the ability to maintain the same shape, size, and sponge property after being implanted for two weeks as was observed prior to implantation; and
exogenous hyaluronic acid (HA) on a surface of the acellular tissue matrix at a concentration which reduces an inflammatory response or fibrosis when the tissue filler is implanted in a body as compared to the same tissue filler not comprising hyaluronic acid.

16. The tissue filler of claim 15, wherein the acellular tissue matrix comprises a dermal matrix.

17. A tissue filler, comprising:
an acellular tissue matrix having a stable three-dimensional structure, having the ability to maintain the same shape, size, and sponge property after being implanted for two weeks as was observed prior to implantation; and
exogenous decorin on a surface of the acellular tissue matrix at a concentration which reduces an inflammatory response or fibrosis when the tissue filler is implanted in a body as compared to the same tissue filler not comprising decorin.

18. The tissue filler of claim 17, wherein the acellular tissue matrix comprises a dermal matrix.

* * * * *